United States Patent
Goff et al.

(10) Patent No.: US 10,562,939 B2
(45) Date of Patent: Feb. 18, 2020

(54) METHOD FOR SIGNIFICANTLY INCREASING LENTIVIRAL PRODUCTION

(71) Applicant: THE TRUSTEES OF COLUMBIA UNIVERSITY IN THE CITY OF NEW YORK, New York, NY (US)

(72) Inventors: Stephen P. Goff, New York, NY (US); Yiping Zhu, New York, NY (US); Liang Tong, New York, NY (US); Shukun Luo, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/093,959

(22) PCT Filed: May 31, 2017

(86) PCT No.: PCT/US2017/035279
§ 371 (c)(1),
(2) Date: Oct. 15, 2018

(87) PCT Pub. No.: WO2017/210337
PCT Pub. Date: Dec. 7, 2017

(65) Prior Publication Data
US 2019/0153038 A1    May 23, 2019

Related U.S. Application Data

(60) Provisional application No. 62/343,797, filed on May 31, 2016.

(51) Int. Cl.

| | |
|---|---|
| A61K 38/00 | (2006.01) |
| A61K 39/00 | (2006.01) |
| C07K 14/005 | (2006.01) |
| C07K 14/02 | (2006.01) |
| C07K 14/05 | (2006.01) |
| C12N 15/113 | (2010.01) |
| C12N 7/00 | (2006.01) |

(52) U.S. Cl.
CPC .............. *C07K 14/005* (2013.01); *C12N 7/00* (2013.01); *C12N 15/1137* (2013.01); *C12Y 114/99003* (2013.01); *C07K 2299/00* (2013.01); *C12N 2310/14* (2013.01); *C12N 2740/10051* (2013.01); *C12N 2740/15022* (2013.01); *C12N 2740/15051* (2013.01); *C12N 2740/16022* (2013.01); *C12N 2740/16051* (2013.01); *C12N 2740/16222* (2013.01)

(58) Field of Classification Search
CPC .. A61K 38/00; A61K 39/00; A61K 2039/525; C07K 14/005; C12Q 2563/143
See application file for complete search history.

(56) References Cited

FOREIGN PATENT DOCUMENTS

EP    2 829 606 A1    1/2015

OTHER PUBLICATIONS

International Search Report and Written Opinion, Appl. No. PCT/US2017/035279, dated Sep. 5, 2017.
Duggal et al., "Evolutionary conflicts between viruses and restriction factors shape immunity," The Journal of Immunology, 12(10):687-695, XP055400911 (2012).
Kurian et al., "Retroviral vectors," J Clin Pathol: Mol Pathol, 53(4):173-176, XP055401090 (2000).
Otto-Wilhelm et al., "Production of lentiviral vectors," Molecular Therapy—Methods & Clinical Development, 3:16017, 14 pages, XP055401120 (2016).
Resh, "HO-2 Pockets Myristoylated Gag," Cell Host & Microbe, 21(2):131-133, XP029913795 (2017).
Zhu et al., "Herne Oxygenase 2 Binds Myristate to Regulate Retrovirus Assembly and TLR4 Signaling," Cell Host & Microbe, 21:220-230, XP029913816 (2017).

Primary Examiner — Barry A Chestnut
(74) Attorney, Agent, or Firm — Leason Ellis LLP

(57) ABSTRACT

Increased viral particle maturation and production can be achieved in various methods for producing viral particles from viral proteins, in general, by inhibiting or preventing Heme Oxygenase 2 (HO-2) from binding to the group-specific antigen (Gag) of the viral proteins, thus allowing delivery of the viral proteins to plasma membranes where they can replicate and mature without interference from HO-2. The increase in viral particle maturation and production can also be achieved by minimizing or eliminating the presence of HO-2 to thus reduce or prevent binding of HO-2 to the group-specific antigen (Gag) of the viral proteins. The invention is particularly applicable to the production of lentiviruses from viral proteins wherein the Matrix domain (MA) of the Gag is myristoylated.

10 Claims, 21 Drawing Sheets

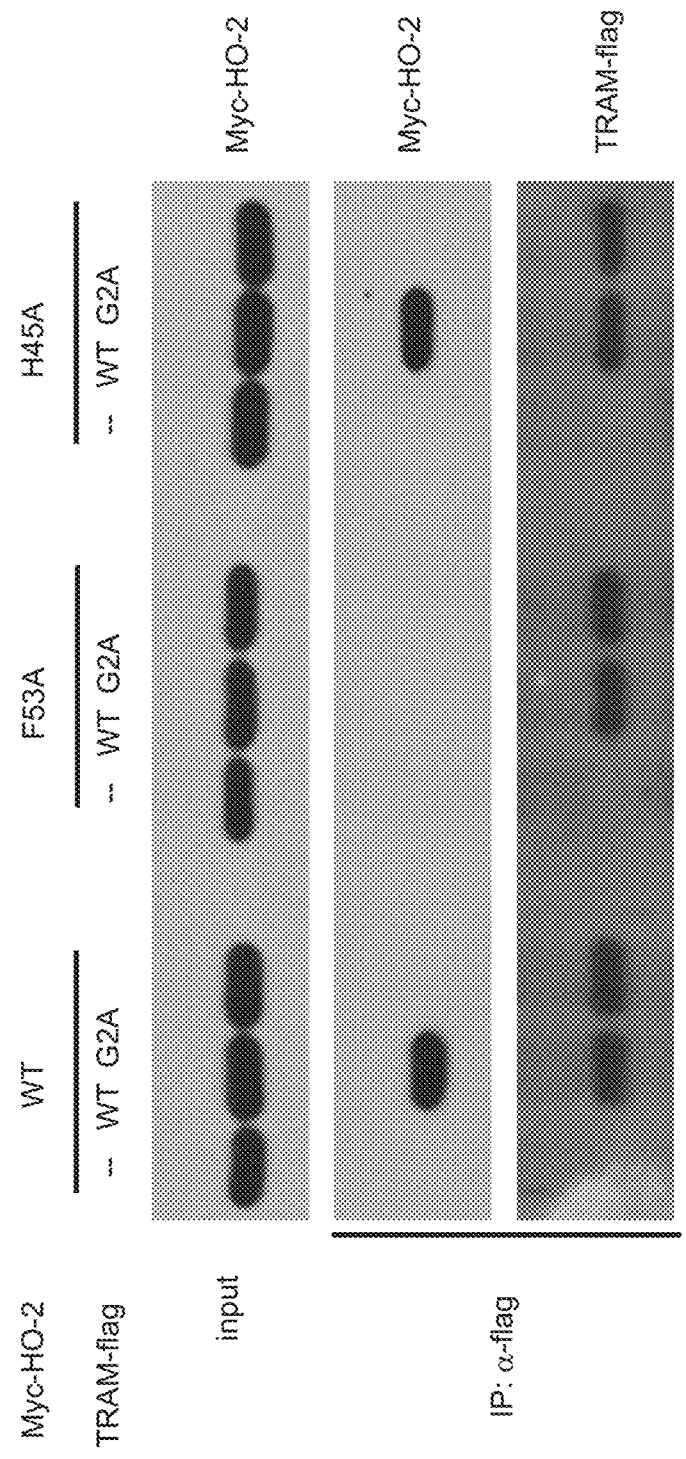

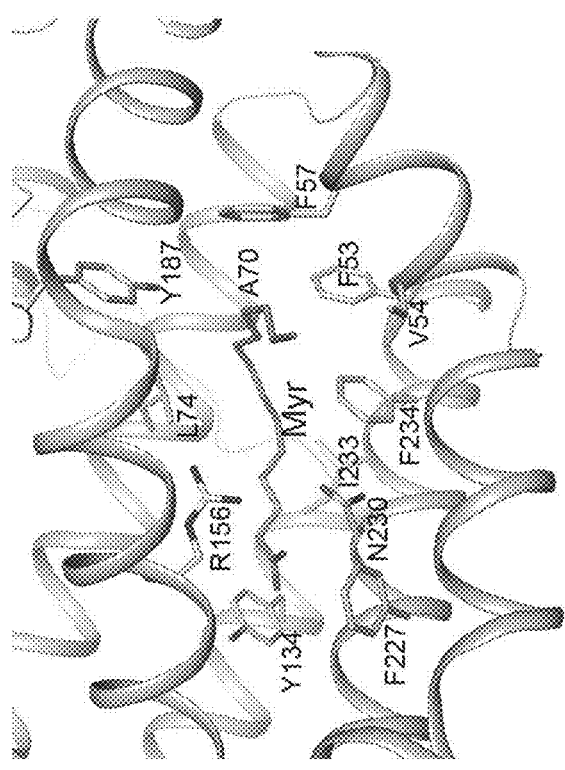
Figure 9A
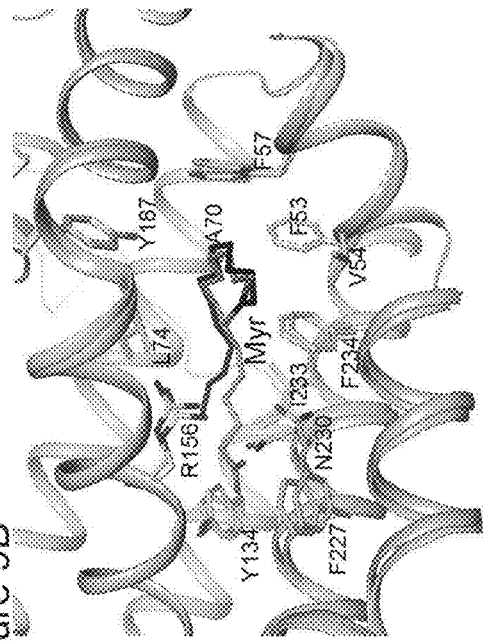
Figure 9B
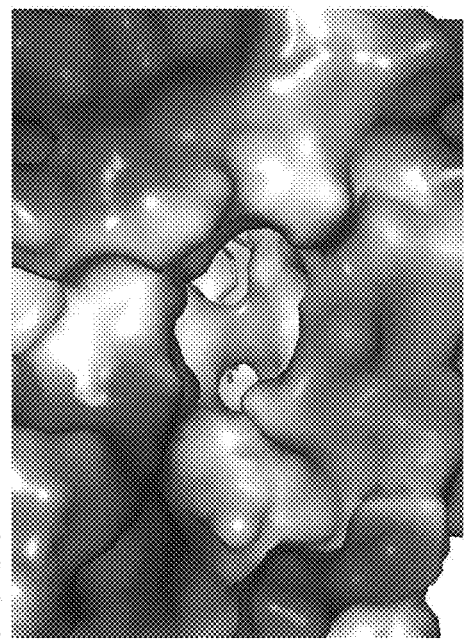
Figure 9D
Figure 9C

| Identified Proteins | EV | HMOX2 | F53A | F57A |
|---|---|---|---|---|
| Heme oxygenase 2 HMOX2 | 132 | 4864 | 5336 | 5737 |
| Extended synaptotagmin-2 ESYT2 | 0 | 14 | 0 | 0 |
| Lamin-B receptor LBR | 0 | 11 | 0 | 0 |
| Keratin, type II cytoskeletal 74 KRT74 | 0 | 11 | 0 | 0 |
| CDGSH iron-sulfur domain-containing protein 2 CISD2 | 0 | 11 | 0 | 0 |
| Translocon-associated protein subunit delta SSR4 | 0 | 10 | 0 | 0 |
| Oxysterol-binding protein-related protein 8 OSBPL8 | 0 | 8 | 0 | 0 |
| Potassium-transporting ATPase alpha chain 1 ATP4A | 0 | 7 | 0 | 0 |
| TIR domain-containing adapter molecule 2 TICAM2 | 0 | 6 | 0 | 0 |
| Reticulon-2 RTN2 | 0 | 5 | 0 | 0 |
| Uncharacterized protein KIAA2013 | 0 | 5 | 0 | 0 |
| SUN domain-containing protein 2 SUN2 | 0 | 5 | 0 | 0 |
| Dephospho-CoA kinase domain-containing protein DCAKD | 0 | 3 | 0 | 0 |
| Solute carrier family 26 member 6 SLC26A6 | 0 | 3 | 0 | 0 |
| Protein 4.1 EPB41 | 0 | 3 | 0 | 0 |
| Carnitine O-palmitoyltransferase 1, liver isoform CPT1A | 0 | 3 | 0 | 0 |
| Xyloside xylosyltransferase 1 XXYLT1 | 0 | 3 | 0 | 0 |
| Protein LYRIC MTDH | 0 | 3 | 0 | 0 |
| 3-ketodihydrosphingosine reductase KDSR | 0 | 3 | 0 | 0 |
| Metallo-beta-lactamase domain-containing protein 2 MBLAC2 | 0 | 3 | 0 | 0 |
| Secretory carrier-associated membrane protein 2 SCAMP2 | 0 | 3 | 0 | 0 |
| Dystrophin DMD | 0 | 2 | 0 | 0 |
| Lipase maturation factor 2 LMF2 | 0 | 2 | 0 | 0 |
| Very long-chain acyl-CoA synthetase SLC27A2 | 0 | 2 | 0 | 0 |
| N-acetylgalactosaminyltransferase 7 GALNT7 | 0 | 2 | 0 | 0 |
| Vesicle-associated membrane protein 7 VAMP7 | 0 | 2 | 0 | 0 |
| Dehydrogenase/reductase SDR family member 13 DHRS13 | 0 | 2 | 0 | 0 |
| Plasma membrane calcium-transporting ATPase 2 ATP2B2 | 0 | 2 | 0 | 0 |
| Vesicle-associated membrane protein 3 VAMP3 | 0 | 2 | 0 | 0 |
| Solute carrier family 41 member 3 SLC41A3 | 0 | 2 | 0 | 0 |

METHOD FOR SIGNIFICANTLY INCREASING LENTIVIRAL PRODUCTION

CROSS-REFERENCE TO RELATED APPLICATIONS

This application is a 371 filing of International Patent Application PCT/US2017/035279 filed May 31, 2017, which claims the benefit of U.S. application No. 62/343,797 filed May 31, 2016.

GOVERNMENT SUPPORT

This invention was made with government support under grants AI106629, GM118093, and CA030488, awarded by the NIH. The government has certain rights in the invention.

BACKGROUND

The present invention relates to a method for significantly increasing lentiviral production by inhibiting or preventing Heme Oxygenase 2 (HO-2) from binding to the group-specific antigen (Gag) of the viral proteins, thus allowing delivery of the viral proteins to plasma membranes for increasing viral particle maturation and production.

A lentivirus is a retrovirus with the ability to deliver significant quantities of viral RNA for integration of a DNA copy of that RNA into the host genome, even into non-dividing cells, making it one of the most efficient vehicles for gene delivery. These and other properties make lentiviruses of particular importance to biotechnology and pharmaceutical industries, and efforts are underway to develop RNA interference technology, gene editing, and long-term stable expression of exogenous genes from lentiviruses.

For example, lentiviruses have proven particularly useful for gene therapies targeting the central nervous and hematopoietic systems (Ginn S L, Alexander I E, Edelstein M L, Abedi M R, Wixon J. Gene therapy clinical trials worldwide to 2012—an update. J Gene Med. 2013 February; 15(2):65-77). Also, lentiviruses have been used for RNA interference, genetic editing, and stable gene expression purposes, by successfully delivering ZFNs, CRISPR/Cas9, luciferases, shRNA, lncRNAs and more (Ginn S L et al, supra; Giacca M, Zacchigna S. Virus-mediated gene delivery for human gene therapy. J Control Release. 2012 Jul. 20; 161(2):377-88; Ausubel L, Couture L, et al. Production of CGMP-Grade Lentiviral Vectors. Bioprocess Int. 2012 February; 10(2): 32-43; and Negre O, et al., Gene Therapy of the β-Hemoglobinopathies by Lentiviral Transfer of the β(A (T87Q))-Globin Gene, Hum Gene Ther. 2016 February; 27(2):148-65. doi: 10.1089/hum.2016.007). By 2012, more than 1,800 gene therapy clinical trials had been undertaken with viruses representing at least 66.8% of all vectors used (Ginn S L et al, supra). Thus, lentiviruses have been successful vectors for the treatment of genetic disease in humans, measurable brain disease, and hematopoietic stem cell therapy (Lenti-Globins). Also, lentiviruses can deliver nucleic acids to a range of host cell lines including mammalian and non-dividing cells (Ginn S L et al, supra; Giacca M et al.). But the ongoing challenge facing commercial and large-volume production of lentiviruses, especially for phase I & II clinical trials, is the inconsistent and low titers (Ausubel L et al. supra).

A major factor limiting the broad application of lentiviruses for these and other purposes is the time and cost required to produce large quantities of viral particles collected from cell lines that can express and synthesize structural proteins for harvesting. N-myristoylation is the covalent attachment of myristic acid, the 14-carbon saturated fatty acid, to the N-terminal glycine of proteins in eukaryotic cells. A large number of proteins of diverse functions are modified by N-myristoylation (Thinon et al., 2014). The addition is catalyzed by N-myristoyltransferases (NMTs), and two isoforms (NMT1 and NMT2) encoded by distinct genes have been identified in mammalian cells (Boutin, 1997; Giang and Cravatt, 1998). Myristoylation is generally permanent and irreversible. NMT1 homozygous knockout mice are not viable, indicating that myristoylation is essential for development (Yang et al., 2005). Myristoylated proteins are involved in a wide variety of physiological activities such as virus replication, cell signaling pathways, oncogenesis, and apoptosis [for review, see (Wright et al., 2010)]. Examples of myristoylated proteins include the retrovirus Gag structural protein (Henderson et al., 1983), tyrosine kinase Src and Src kinase family members (Cross et al., 1984), phosphatases such as calcineurin B (Aitken et al., 1982), the BH3 domain protein BID (a key mediator of apoptosis) (Zha et al., 2000), and TRAM (Toll-like receptor adaptor molecule, aka TICAM2), a mediator of TLR4 signaling (Rowe et al., 2006). Many, but not all, myristoylated proteins reside in intracellular membranes.

The Gag and Gag-Pol precursor proteins of nearly all retroviruses are modified by the cotranslational addition of myristate to the amino-terminal glycine of the matrix domain (MA) (Gottlinger et al., 1989; Henderson et al., 1983; Palmiter et al., 1978). The avian alpharetroviruses are exceptions to the rule, and instead their Gag and Gag-Pol proteins are modified by N-terminal acetylation. The N-myristoylation of all other Gags is essential for replication of these retroviruses, and inhibition of the NMT's enzymatic activity or mutation of the Gag N-terminal glycine to alanine to prevent myristoylation blocks the spread of virus in host cells (Bryant and Ratner, 1990; Gottlinger et al., 1989; Rein et al., 1986). When Gag myristoylation is prevented, the Gag protein remains in the cytoplasm and is not properly delivered to the plasma membrane for virion assembly and budding (Bryant and Ratner, 1990; Ono and Freed, 1999). Mutational studies have revealed that the N-terminal myristate, and also a cluster of basic amino acids constituting a small basic patch on the surface of MA, are both required for membrane binding of Gag (Resh, 2005). The basic residues of Gag are thought to interact with the negatively charged phospholipids of the plasma membrane to promote its membrane association (Hill et al., 1996). It has been proposed that in the cytoplasm the N-terminal myristate of Gag is initially trapped by a hydrophobic pocket in the MA domain, limiting the interaction between Gag and endogenous membranes, and conformational changes (a "myristoyl switch") associated with virus maturation expose the myristate (Hermida-Matsumoto and Resh, 1999; Resh, 2004). The plasma membrane-specific lipid PI(4,5)P2 can compete with myristate for binding to the hydrophobic pocket, promoting the exposure and insertion of the myristate tail into the plasma membrane and thus facilitating virus budding (Bouamr et al., 2003; Saad et al., 2007; Zhou and Resh, 1996). The bulk of the MA domain is not absolutely required for membrane association and virion budding. An HIV-1 Gag mutant lacking most of MA and a portion of CA, but retaining the N-terminal myristoylation (so-called "miniGag") can efficiently mediate virion assembly and release (Accola et al., 2000; Reil et al., 1998), suggesting that the exposure and insertion of the myristate tail is the primary determinant for the membrane association of Gag and virus budding.

It has long been supposed that there must be proteins that bind myristoylated substrates and regulate their localization and function, but few have been identified. UNC119 is a lipid-binding protein of photoreceptors (Higashide and Inana, 1999; Swanson et al., 1998) that interacts with acylated rod photoreceptor transducin α subunit (Tα) and myristoylated ciliopathy protein nephrocystin-3 (NPHP3) (Constantine et al., 2012; Wright et al., 2011; Zhang et al., 2011). An early search revealed a protein of 32 kDa that bound to a myristoylated v-Src peptide (Resh and Ling, 1990), but its identity has not previously been established.

The present invention now has discovered how to increase the production of large quantities of lentivirus particles that are assembled from proteins that have been myristoylated or that carry other acyl chains of fatty acids. The method thus addresses the need for such increased production.

SUMMARY OF THE INVENTION

The invention now discloses that increased viral particle maturation and production can be achieved by various methods of manipulation of cells that are utilized to produce viral particles. This is achieved, in general, by inhibiting or preventing Heme Oxygenase 2 (HO-2) from binding to the group-specific antigen (Gag) of the viral proteins, thus allowing delivery of the viral proteins to plasma membranes where they can replicate and mature without interference from HO-2. The invention also can increase viral particle maturation and production by minimizing or eliminating the presence of HO-2 to thus reduce or prevent binding of HO-2 to the group-specific antigen (Gag) of the viral proteins.

The invention in particular is applicable to the production of lentiviruses from viral proteins wherein the Matrix domain (MA) of the Gag of the protein carries a C14 myristate modification. As noted herein, a large number of proteins of diverse functions are modified by N-myristoylation, and the invention increases the production of lentiviruses from such proteins by inhibiting or removing HO-2 from the producer cells.

Typically, the HO-2 is depleted from the producer cell so that it cannot interfere with the lentivirus production process. In these methods, the inhibition, reduction or prevention of HO-2 binding is typically achieved by genetic knockdown, e.g., by preparation of a suitable siRNA or construction of an shRNA expression plasmid, followed by the transfection of one of these constructs into cultured cells. The methods can alternatively comprise deleting or knocking out the HO-2 gene in producer cell lines, or introducing mutations in the HO-2 gene that alter the hydrophobic channel.

Alternatively, the inhibition, reduction or prevention of HO-2 binding can be achieved by pharmaceutical inhibition of binding of the HO-2 protein to the target protein. This is achieved by adding a heme analog to living cells, for inhibition of HO-2 myristate binding. A useful heme analog is a transition metal protoporphyrin (e.g., tin protoporphyrin).

All of the foregoing methods result in interference with HO-2 binding to the Gag of the viral proteins, thus allowing significantly increased production of lentiviruses.

BRIEF DESCRIPTION OF THE DRAWING FIGURES

Other features and advantages of the present invention can be discerned from the following detailed description which is provided in conjunction with the appended drawing figures, wherein:

FIGS. 1A, 1B, 1C and 1D are Western blot diagrams which illustrate that HO-2 is a myristate-binding protein, wherein:

FIG. 1A illustrates that the interaction between HO-2 and HIV-1 MA is dependent on the N-myristoylation of MA. 293A-FH (MA-flag−), 293A-MA-FH (MA-flag WT), or 293A-MAG2A-FH (MA-flag G2A) cells were transfected with pCMV-Myc-HO-2. Cell lysates were subjected to immunoprecipitation using anti-flag antibody beads. Myc-HO-2 and MA-flag were detected by Western blot using anti-Myc and anti-flag antibodies, respectively.

FIG. 1B shows that endogenous HO-2 interacts with wild type HIV-1 MA (WT), but not HIV-1 MA with the G2A mutation. The cell lysates of 293A-FH (MA-flag−), 293A-MA-FH (MA-flag WT), or 293A-MAG2A-FH (MA-flag G2A) cells were subjected to immunoprecipitation using anti-flag antibody beads. The endogenous HO-2 was detected by specific HO-2 antibody.

FIG. 1C illustrates that HO-2 interacts with different myristoylated proteins. 293A cells expressing an empty vector (293A-FH (EV), or flag-tagged versions of wild-type HIV-1 MA (293A-MA-FH), or HIV-1 MA with a G2A mutation (293A-MAG2A-FH), or wild-type MLV MA (293A-MMA-FH), or MLV MA with a G2A mutation (293A-MMAG2A-FH), or wild-type v-Src (293A-vSrc-FH), or v-Src with a G2A mutation (293A-vSrcG2A) were transfected with pCMV-Myc-HO-2. Cell lysates were subjected to immunoprecipitation using anti-flag antibody beads. Myc-HO-2 and different flag tagged myristoylated proteins were detected by Western blot using anti-Myc and anti-flag antibodies, respectively.

FIG. 1D demonstrates that myristic acid competes with HIV-1 MA for binding to HO-2. 293A-FH (MA-flag−) or 293A-MA-FH (MA-flag+) cells were transfected with pCMV-Myc-HO-2. Cell lysates were added with indicated amount of myristic acid and then subjected to immunoprecipitation using anti-flag antibody beads. Myc-HO-2 and MA-flag were detected by Western blot using anti-Myc and anti-flag antibodies respectively, while RRS was detected by specific RRS antibody. For all co-immunoprecipitation assays, 5% of the total cell lysates were used as input. IP: immunoprecipitation. See also FIG. 8.

FIGS. 2A, 2B, 2C, 2D, 2E, 2F and 2G illustrate crystal structures of human HO-2 in complex with myristate and laurate, wherein:

FIG. 2A is a schematic drawing of the structure of HO-2 in complex with myristate. HO-2 is shown as ribbons (light cyan) and myristate as spheres (black for carbon atoms, red for oxygen). All structure figures were produced with PyMOL (www.pymol.org).

Figure 2A:
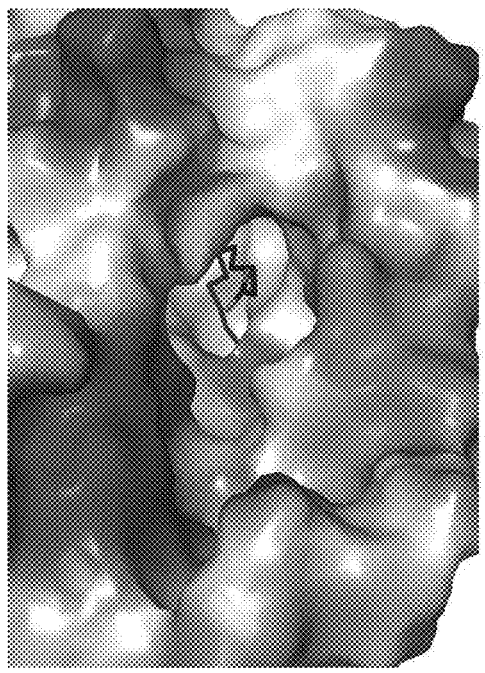
FIG. 2B shows the molecular surface of HO-2 in the myristate binding site, colored by electrostatic potential.
FIG. 2C is a structural drawing showing detailed interactions between myristate (black) with HO-2 (light cyan).
FIG. 2D shows that omitting $F_o$-$F_c$ electron density at 1.9 Å resolution for myristate in FIG. 1A, is contoured at 2.5σ and the density for the carboxylate group becomes visible at 2σ.
FIG. 2E is a structural drawing showing detailed interaction between laurate and HO-2.
FIG. 2F shows the "omitting $F_o$-$F_c$ electron density" at 2.1 Å resolution for laurate in FIG. 2E is contoured at 2.5σ.
Figure 2B:
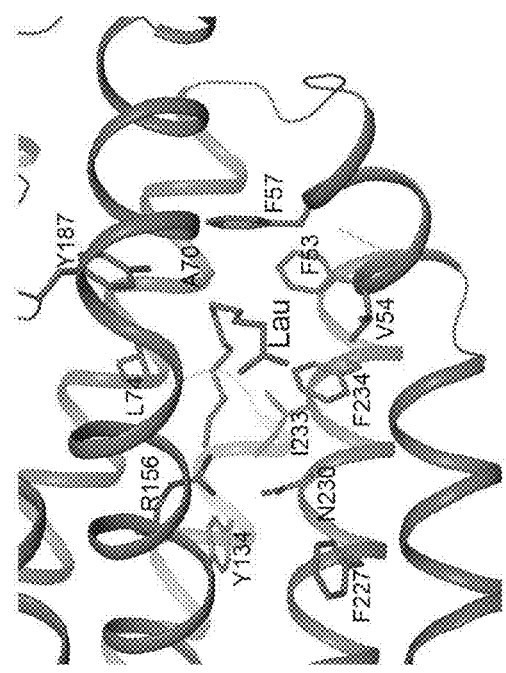
Figure 2C:
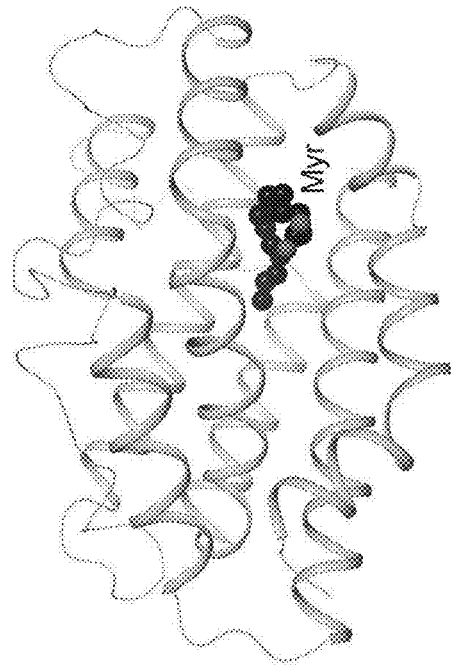
Figure 2E:
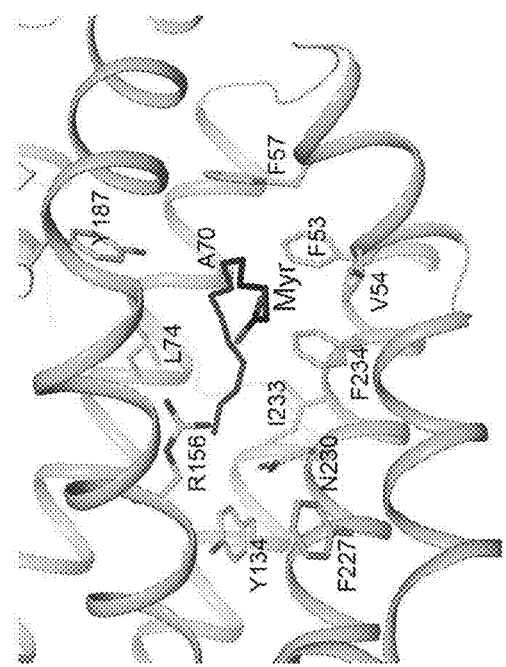
Figure 2F:
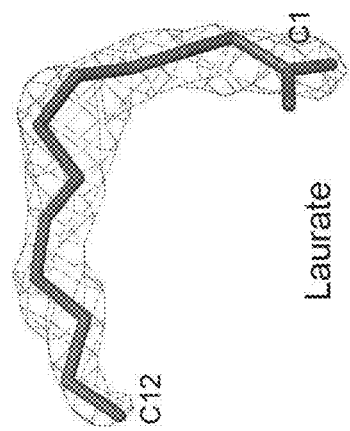
Figure 2D:
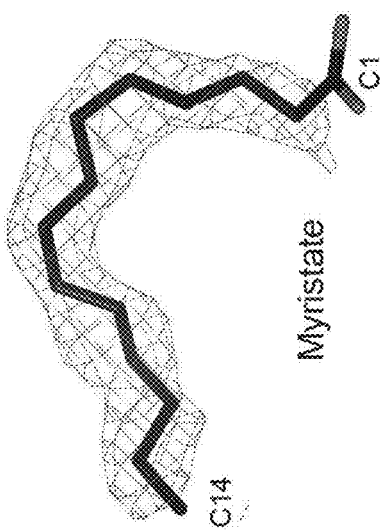
Figure 2G:
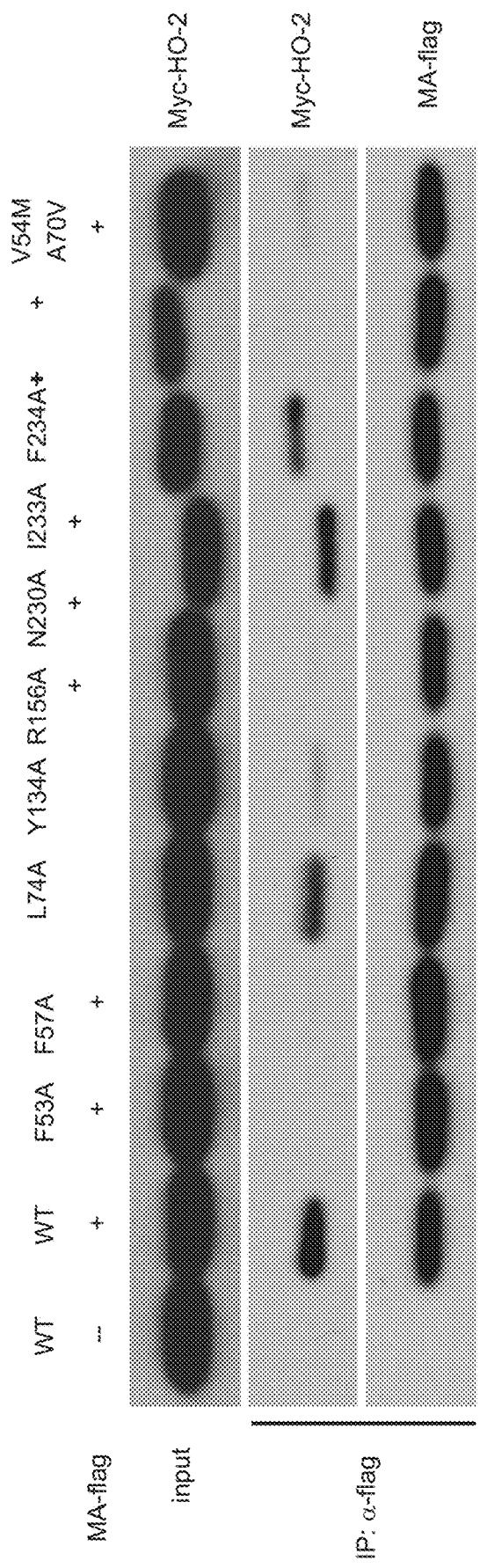

FIG. 2G shows the identification of the residues in HO-2 that are essential for its myristate-binding activity. 293A-FH (MA-flag−) or 293A-MA-FH (MA-flag+) cells were transfected with pCMV-Myc-HO-2 expressing wild type (WT) HO-2 or HO-2 bearing indicated mutations. Cell lysates were subjected to immunoprecipation using anti-flag antibody beads. Myc-HO-2 and MA-flag were detected by Western blot using anti-Myc and anti-flag antibodies respectively. 5% of the total cell lysate were used as input. IP: immunoprecipitation. See also FIG. 9.

Figure 3A:
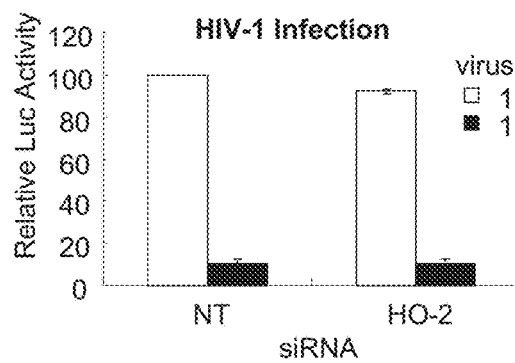

FIGS. 3A, 3B, 3C, 3D, 3E, 3F, and 3G show that knockdown of HO-2 enhances the production of retrovirus with N-myristoylation modification, wherein:

FIG. 3A shows that HO-2 does not affect the infection of HIV-1. 293A cells were transfected twice with a control non-targeting siRNA (NT) or a siRNA pool against HO-2 (siRNA HO-2) and then infected with VSVG pseudotyped NL4-3luc virus at 1:10 or 1:100 dilution. Luciferase activities were measured 48 hours after infection. The luciferase activity from cells transfected with control siRNA (NT) and infected with 1:10 diluted virus was set as 100. The data are means+/−SD from three independent experiments.

Figure 3B:
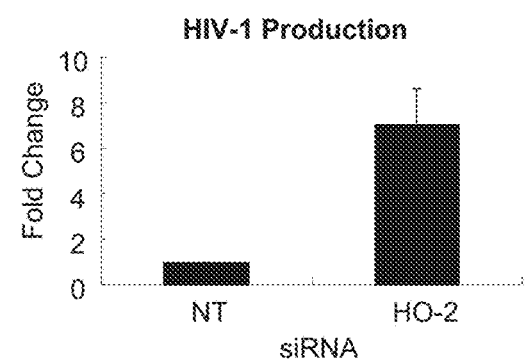

FIG. 3B illustrates that knockdown of HO-2 enhances the production of infectious HIV-1 virus. 293A cells were transfected twice with the control non-targeting siRNA (NT) or a siRNA pool against HO-2 (siRNA HO-2) and then transfected with pNL4.3luc and pVSVG to package virus. 48 hours after plasmids transfection, same amounts of the supernatant from transfected cells were used to infect 293A cells. Luciferase activities were measured 48 hours after infection. The luciferase activity from cells infected with virus packaged from control siRNA (NT) transfected cells was set as 1. The data are means+/−SD from three independent experiments.

Figure 3C:
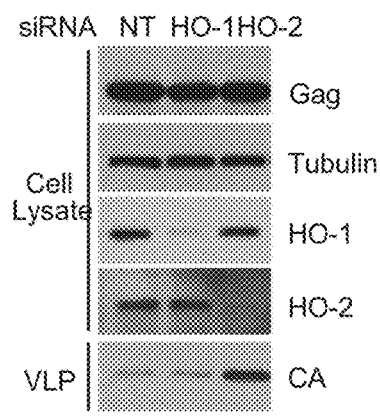

FIG. 3C shows that knockdown of HO-2, but not HO-1, increased the release of HIV-1 Gag from 293A cells. 293A cells were transfected twice with the control non-targeting siRNA (NT) or the siRNA pool against HO-2 (siRNA HO-2) or HO-1 (siRNA HO-1) and then transfected with pNL4.3luc and pVSVG to package virus. 48 hours after plasmids transfection, virus-like particles (VLP) were pelleted from supernatant of cells. Gag expression in the cells (cell lysate) and CA in the VLP were detected by HIV-1 p24 antibody.

Figure 3D:
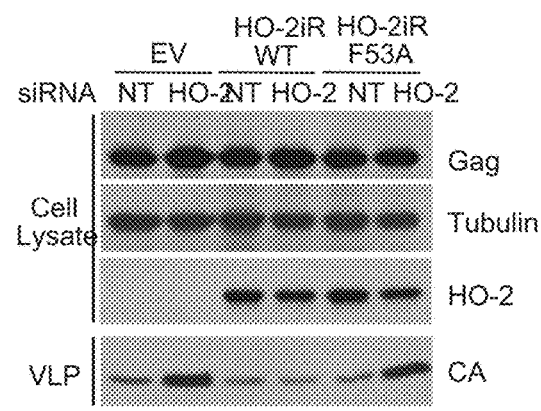

FIG. 3D illustrates that HO-2's myristate-binding activity inhibits the release of HIV-1 Gag from 293A cells. 293A-FH, 293A-HO-2iR (siRNA resistant HO-2), or 293A-HO-2iR-F53A (siRNA resistant HO-2 deficient in myristate-binding activity) cells were transfected twice with the control non-targeting siRNA (NT) or the siRNA pool against HO-2 (siRNA HO-2) and then transfected with pNL4.3luc. 48 hours after plasmids transfection, virus-like particles (VLP) were pelleted from supernatant of cells. Gag expression in the cells (cell lysate) and CA in the VLP were detected by HIV-1 p24 antibody.

Figure 3E:
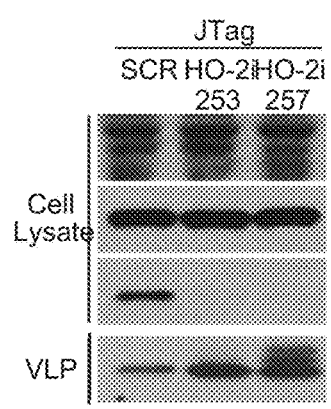

FIG. 3E shows that knockdown of HO-2 increases the release of HIV-1 Gag from Jurkat T cells. JTag-SCR, JTag-HO-2i253, JTag-HO-2i257 cells were transfected with pNL4.3luc. 48 hours after transfection, virus-like particles (VLPs) were pelleted from supernatant of cells. Gag expression in the cells (cell lysate) and CA in the VLP were detected by HIV-1 p24 antibody.

Figure 3F:
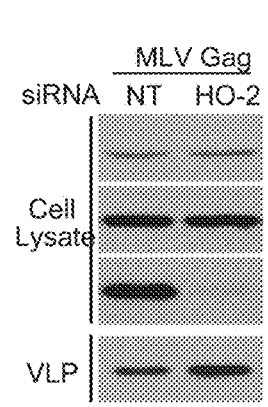
Figure 3G:
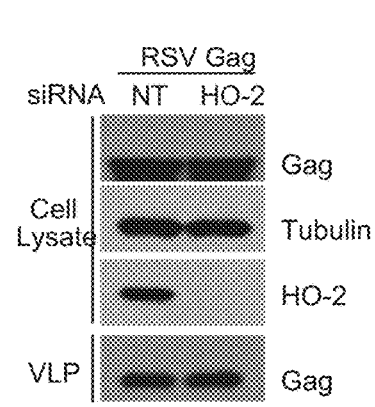

FIGS. 3F and 3G demonstrate that knockdown of HO-2 increases the release of MLV Gag, but not RSV Gag (without N-myristoylation), from 293A cells. 293A cells were transfected twice with the control non-targeting siRNA (NT) or the siRNA pool against HO-2 (siRNA HO-2) and then transfected with pHIT60 (expressing MLV Gag) (FIG. 3F) or pCMV-RSVGag (FIG. 3G). 48 hours after transfection, virus-like particles (VLPs) were pelleted from supernatant of cells. Gag expression in the cells (cell lysate) and CA in the VLP were detected by specific antibodies against MLV Gag (FIG. 3F) or RSV Gag (FIG. 3G). See also FIG. 10.

Figure 4A:
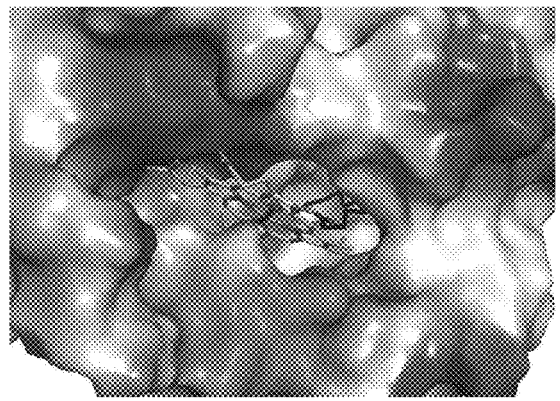
Figure 4B:
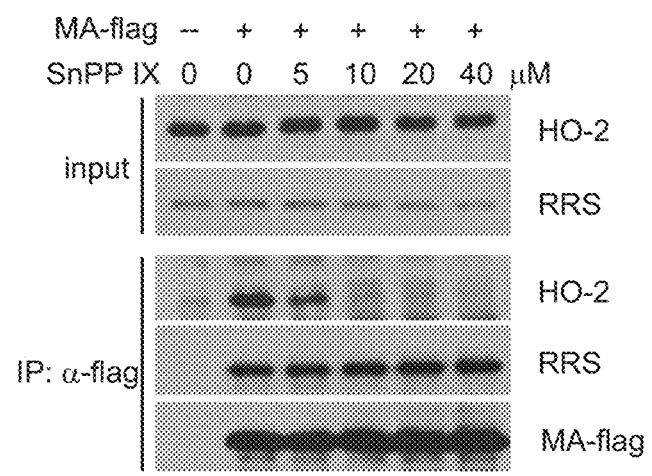
Figure 4C:
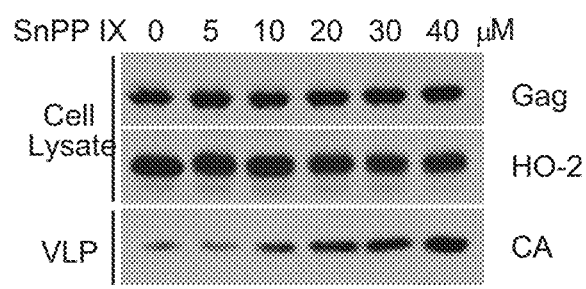

FIGS. 4A, 4B and 4C illustrate that SnPP IX inhibits HO-2's myristate-binding activity, wherein:

FIG. 4A shows that the molecular surface of HO-2 active site and myristate binding site, colored by electrostatic potential. The bound position of heme is predicted to clash with that of myristoylated proteins (myristate in black).

FIG. 4B shows that heme analog SnPP IX inhibits HO-2's binding to HIV-1 MA. 293A-FH (MA-flag−) or 293A-MA-FH (MA-flag+) cells were treated with indicated concentrations of SnPP IX for 48 hours. Cell lysates were subjected to immunoprecipitation using anti-flag antibody beads. Endogenous HO-2 and MA-flag were detected by Western blot using anti-HO-2 and anti-flag antibodies respectively, while RRS was detected by specific RRS antibody. For all the co-ip assay, 5% of the total cell lysate were used as input. IP: immunoprecipitation.

FIG. 4C shows that heme analog SnPP IX increases the yield of virus particles by inhibiting HO-2 myristate binding. 293A cells were transfected with pNL4.3luc and treated with SnPP IX at indicated concentrations for 48 hours. Virus-like particles (VLPs) were pelleted from supernatant of cells. Gag expression in the cells (cell lysate) and CA in the VLP were detected by HIV-1 p24 antibody. See also FIG. 1.

Figure 5A:
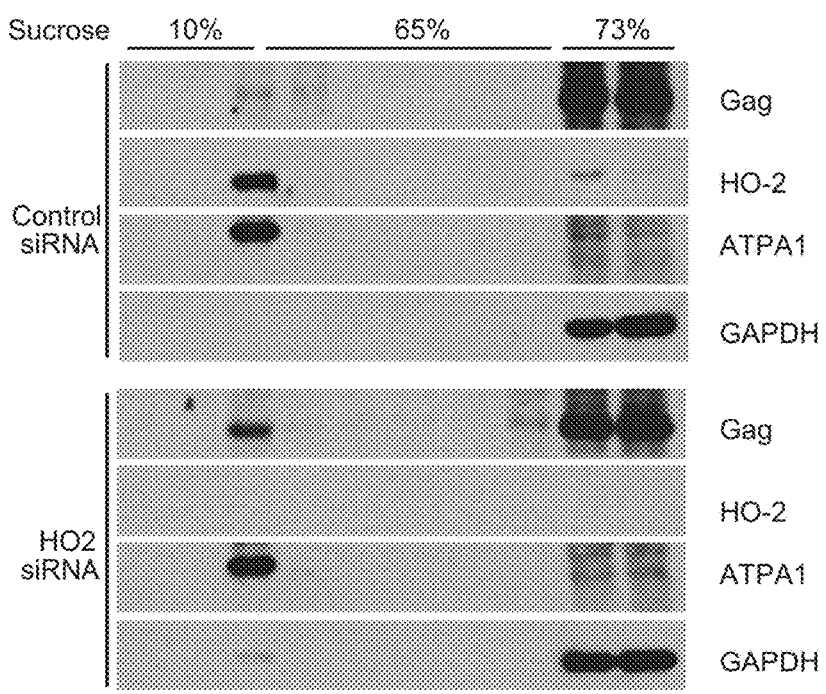
Figure 5B:
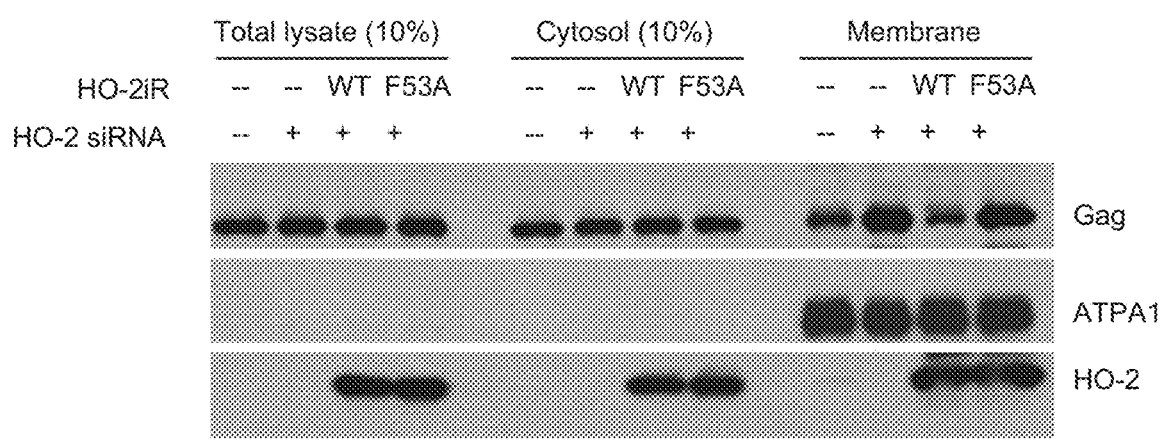

FIGS. 5A and 5B demonstrate that HO-2 inhibits the membrane association of HIV-1 Gag, wherein:

FIG. 5A shows that knockdown of HO-2 enhance membrane association of HIV-1 Gag. 293A cells were transfected twice with the control non-targeting siRNA (NT) or the siRNA pool against HO-2 (siRNA HO-2) and then were transfected with pNL4.3luc. 48 hours after transfection, membrane floatation assay was performed to examine the distribution of Gag in the cytosol and membrane fraction. ATPA1 is the membrane fraction marker, while GAPDH is the cytosol fraction marker.

FIG. 5B shows that HO-2's myristate-binding activity inhibits the membrane association of HIV-1 Gag. 293A-FH, 293A-HO-2iR (siRNA resistant HO-2), or 293A-HO-2iR-F53A (siRNA resistant HO-2 deficient in myristate-binding activity) cells were transfected twice with the control non-targeting siRNA (NT) or the siRNA pool against HO-2 (siRNA HO-2) as indicated and then cells were transfected with pNL4.3luc. 48 hours after transfection, cell lysates were subjected to cell fractionation and the subcellular distribution of Gag were detected by Western blot using HIV-1 p24 antibody. ATPA1 is the membrane fraction marker.

FIGS. 6A, 6B, 6C, 6D, and 6E illustrate that HO-2 acts as a negative feedback regulator of TRAM-dependent LPS-TLR4 pathway via its myristate-binding activity, wherein:

FIG. 6A shows that the interaction between HO-2 and TRAM is dependent on the N-myristoylation of TRAM. 293A-FH (TRAM-flag−), 293A-TRAM-FH (TRAM-flag WT), or 293A-TRAMG2A-FH (TRAM-flag G2A) cells were transfected pCMV-Myc-HO-2 (HO-2 WT), pCMV-Myc-HO-2F53A (HO-2 F53A), or pCMV-Myc-HO-2H45A (HO-2 H45A). Cell lysates were subjected to immunoprecipitation using anti-flag antibody beads. Myc-HO-2 and TRAM-flag were detected by Western blot using anti-Myc and anti-flag antibodies, respectively. (B) Knockout of HO-2 enhances TRAM's activity. 293A-Control, 293A-HO-2KO#1, and 293A-HO-2KO#6 cells were transfected with 0.1 μg pRANTES-Luc, 0.1 μg pRL-TK, and indicated amounts of pEF-BOS-TRAM-flag. (Upper panel)

Luciferase activities were measured 24 hours after transfection. The luciferase activity from 293A-Control cells without TRAM transfection was set as 1. The data are means+/−SD from three independent experiments. (Lower panel) The expression of HO-2 in HO-2 knockout cell lines was examined by Western blot.

Figure 6B:
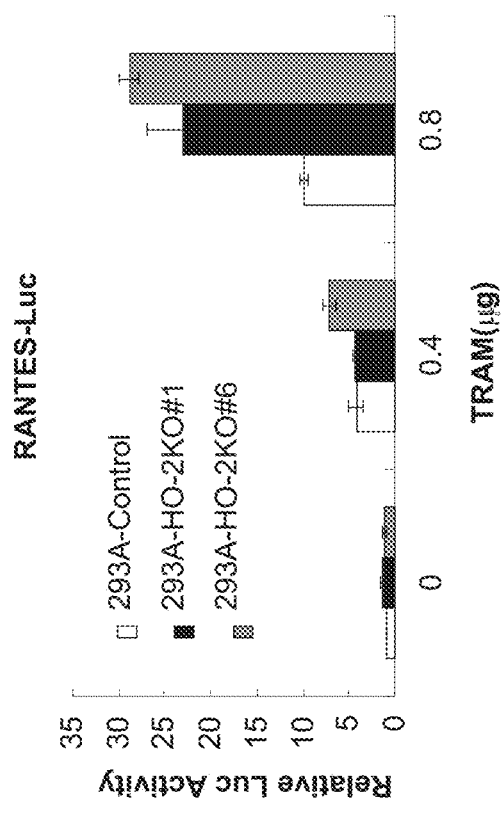
Figure 6C:
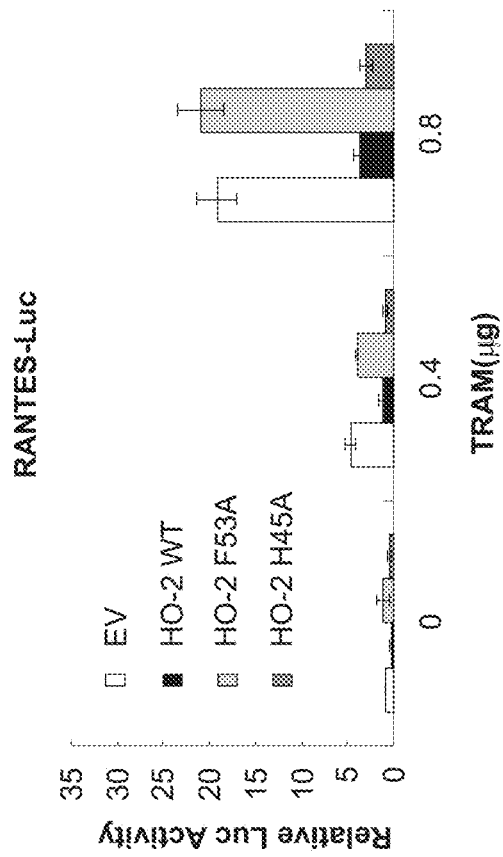

FIG. 6C shows that HO-2's myristate-binding activity, but not its heme oxygenase activity inhibits TRAM's function to activate RANTES promoter. 293A-HO-2KO#6-FH (EV), 293A-HO-2KO#6-HO-2 (HO-2 WT), 293A-HO-2KO#6-HO-2-F53A (HO-2 F53A), 293A-HO-2KO#6-HO-2-H45A (HO-2 H45A) cells were transfected with 0.1 μg pRANTES-Luc, 0.1 μg pRL-TK, and indicated amounts of pEF-BOS-TRAM-flag. (Upper panel) Luciferase activities were measured 24 hours after transfection. The luciferase activity from 293A-HO-2KO#6-FH (EV) cells without TRAM transfection was set as 1. The data are means+/−SD from three independent experiments. (Lower panel) The expression of HO-2 in cells was examined by Western blot.

Figure 6D:
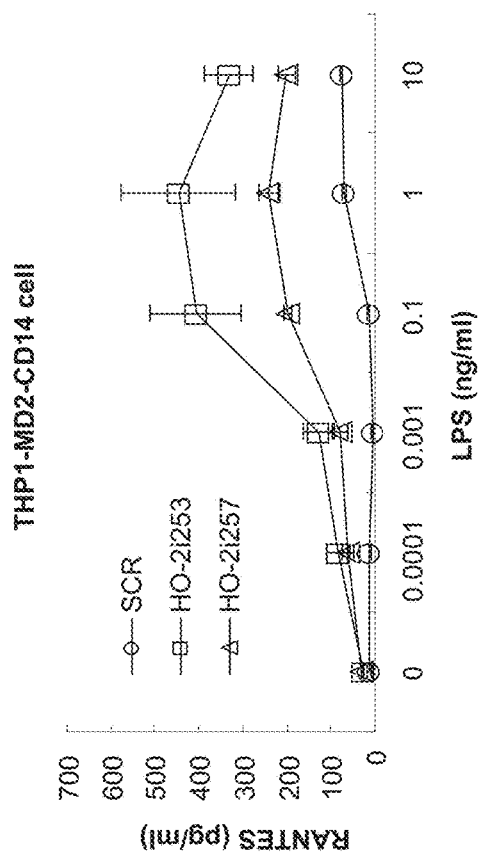

FIG. 6D shows that knockdown of HO-2 enhances the expression of RANTES induced by LPS. THP-1-MD2-CD14-SCR, THP-1-MD2-CD14-HO-2i253, and THP-1-MD2-CD14-HO-2i257 were treated with indicated concentration of LPS for 24 hour. The levels of RANTES in the supernatant were measured by ELISA kit. The data are means+/−SD from three independent experiments.

Figure 6E:
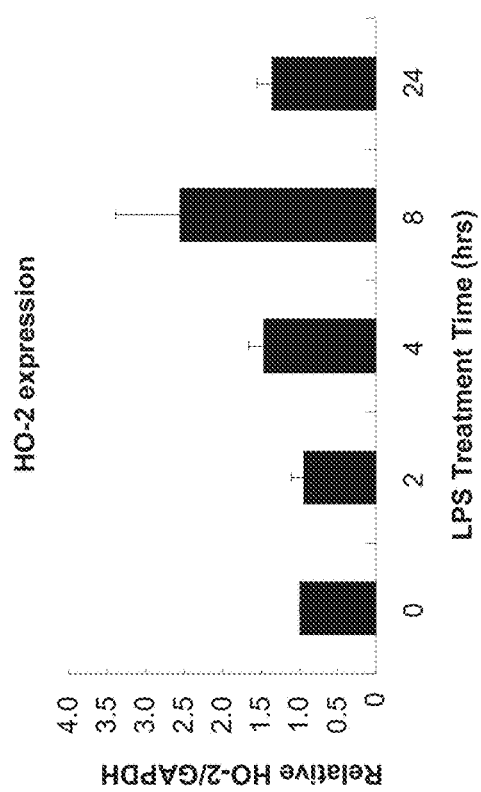

FIG. 6E shows that LPS induces the expression of HO-2. THP-1-MD2-CD14 cells were treated with 10 ng/ml LPS for indicated time. Total RNA was extracted from cells, and real time PCR was performed to measure the levels of HO-2 mRNA. The levels of HO-2 mRNA were normalized to that of GAPDH and the level of HO-2 mRNA in LPS untreated cells was set as 1. The data are means+/−SD from three independent experiments. See also FIG. 12.

Figure 7A:
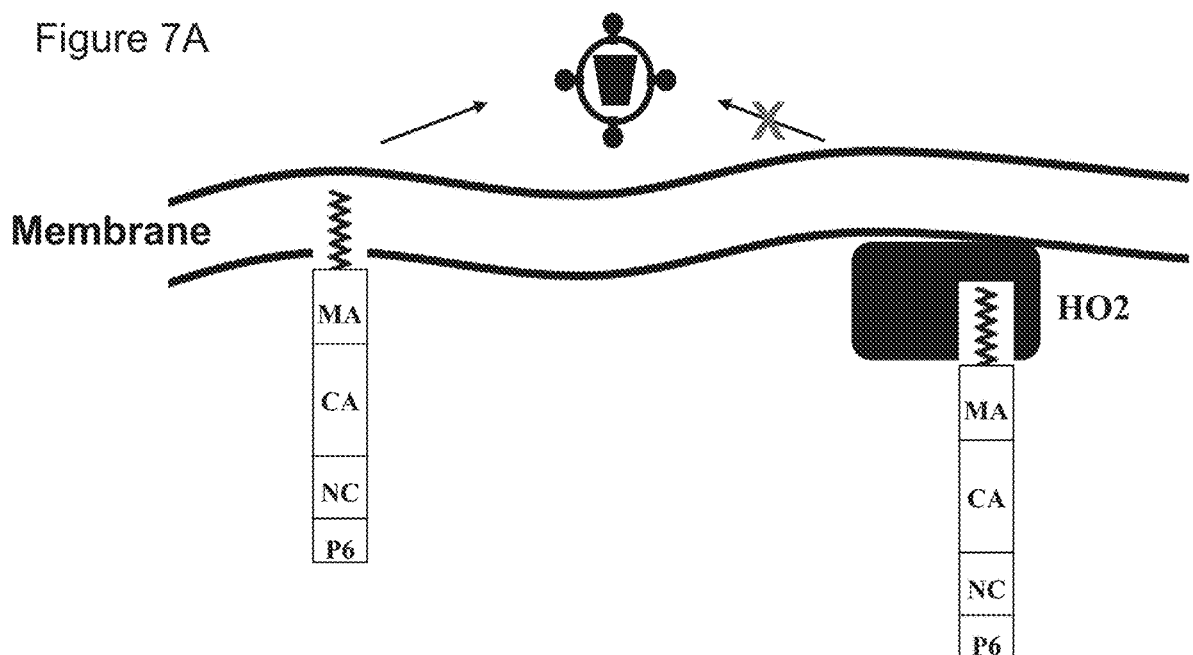
Figure 7B:
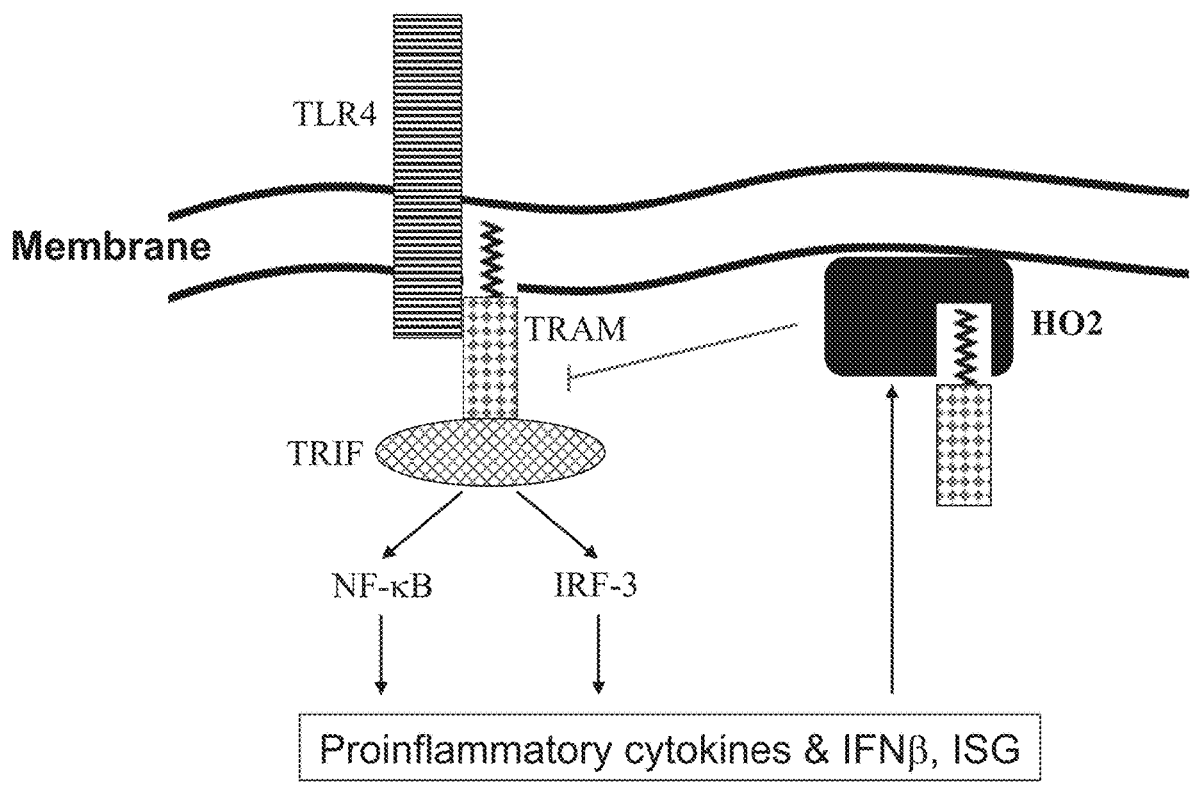

FIGS. 7A and 7B provide a working model for HO-2, wherein:

FIG. 7A illustrates the binding of HO-2 to the N-terminal myristate of HIV-1 Gag traps the myristate moiety and prevents it from inserting in its proper conformation into the membrane, and thus inhibits HIV-1 virion production.

FIG. 7B illustrates that HO-2 binds to the N-terminal myristate moiety and down regulating the function of TRAM. HO-2 is induced by LPS-TLR4 signaling and acts as a negative feedback regulator of the LPS-TLR4 pathway.

Figure 8A:
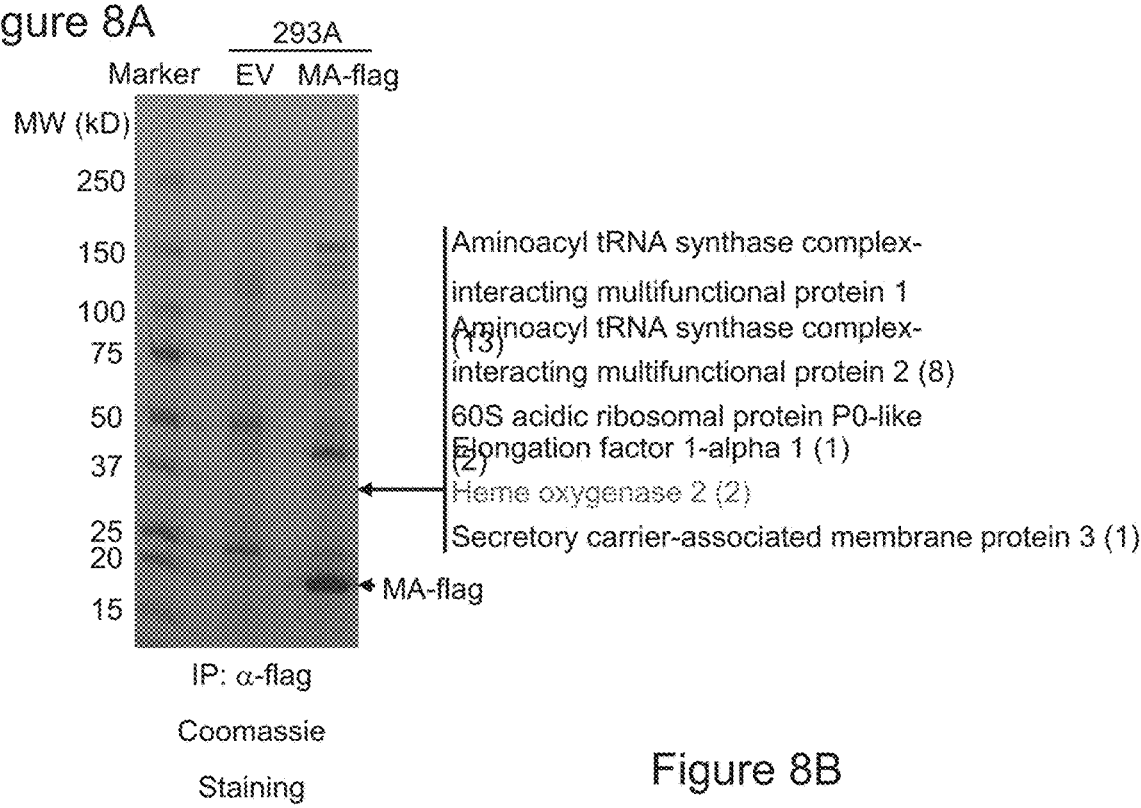
Figure 8B:
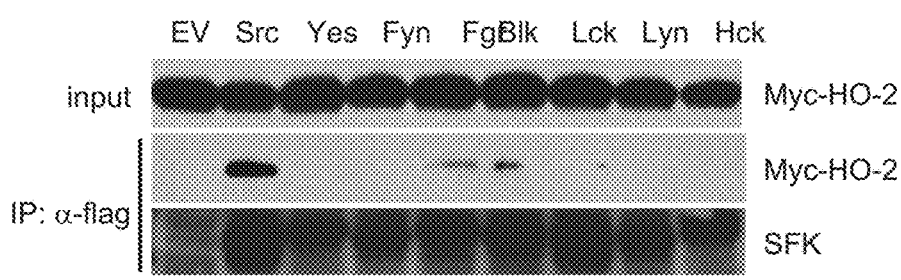
Figure 8C:
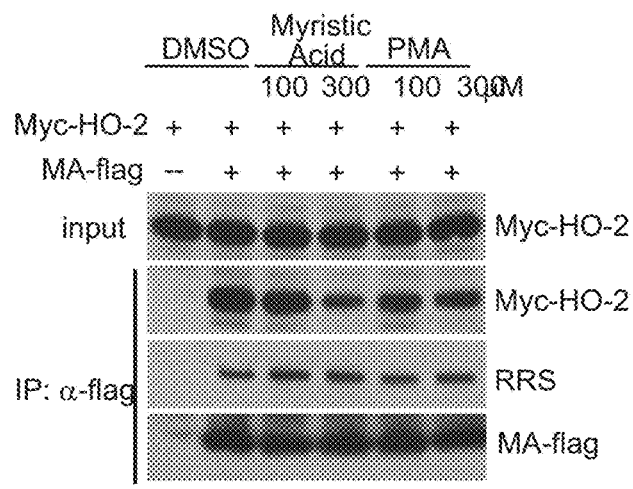

FIGS. 8A, 8B and 8C illustrate electrophoresis results for binding of HO-2 to myristoylated proteins, with FIG. 8A providing Coomassie staining results and FIGS. 9B and 9C providing Western blot diagrams.

Figure 9E:
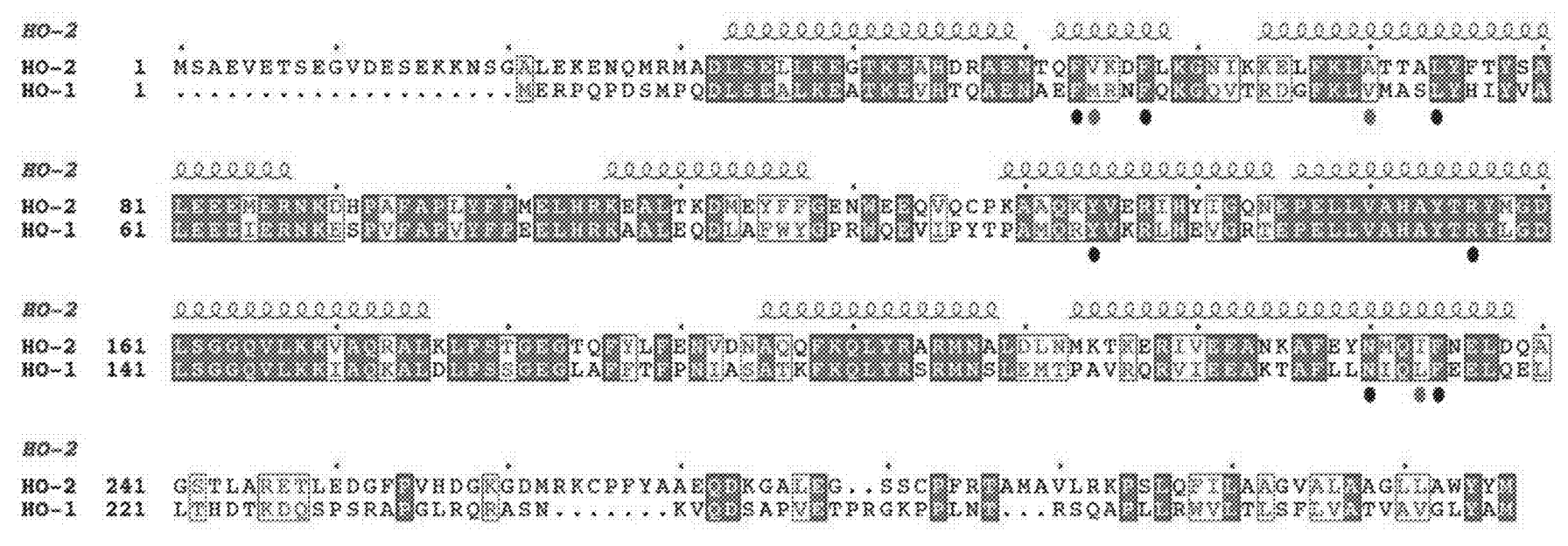
Figure 9G:
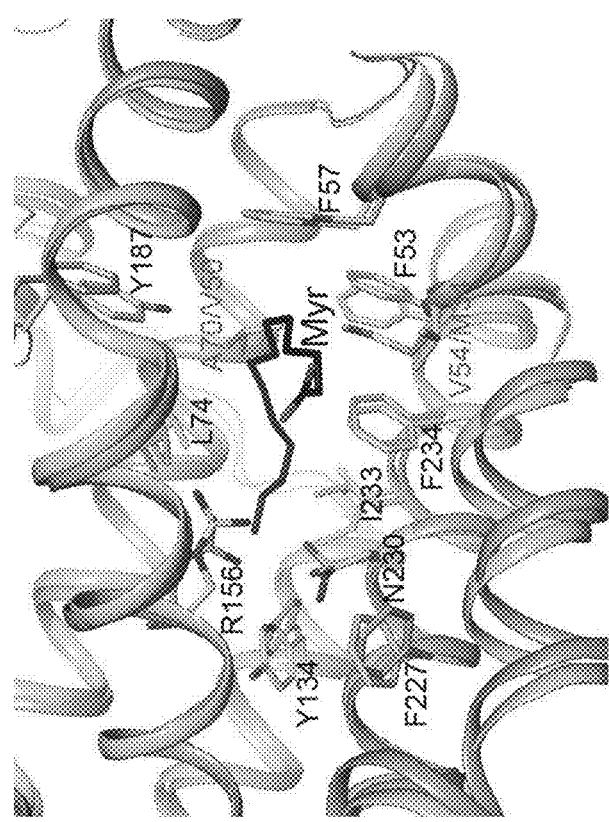
Figure 9F:
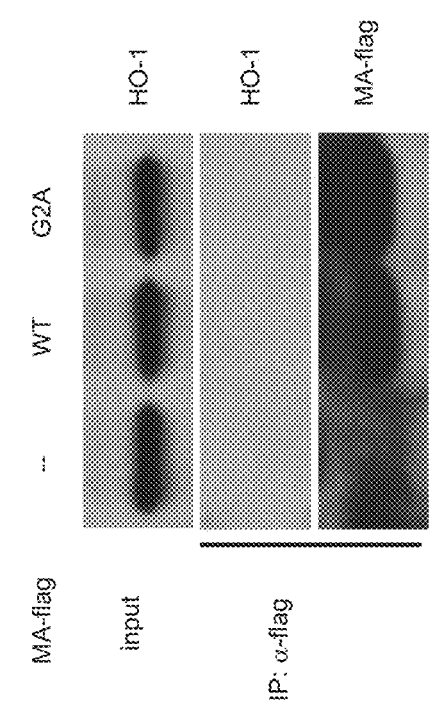

FIGS. 9A, 9B, 9C, 9D, and 9G are models of how myristyl binding to the protein and FIG. 9E being a sequence identification and FIG. 9F being a Western blot diagram.

Figure 10A:
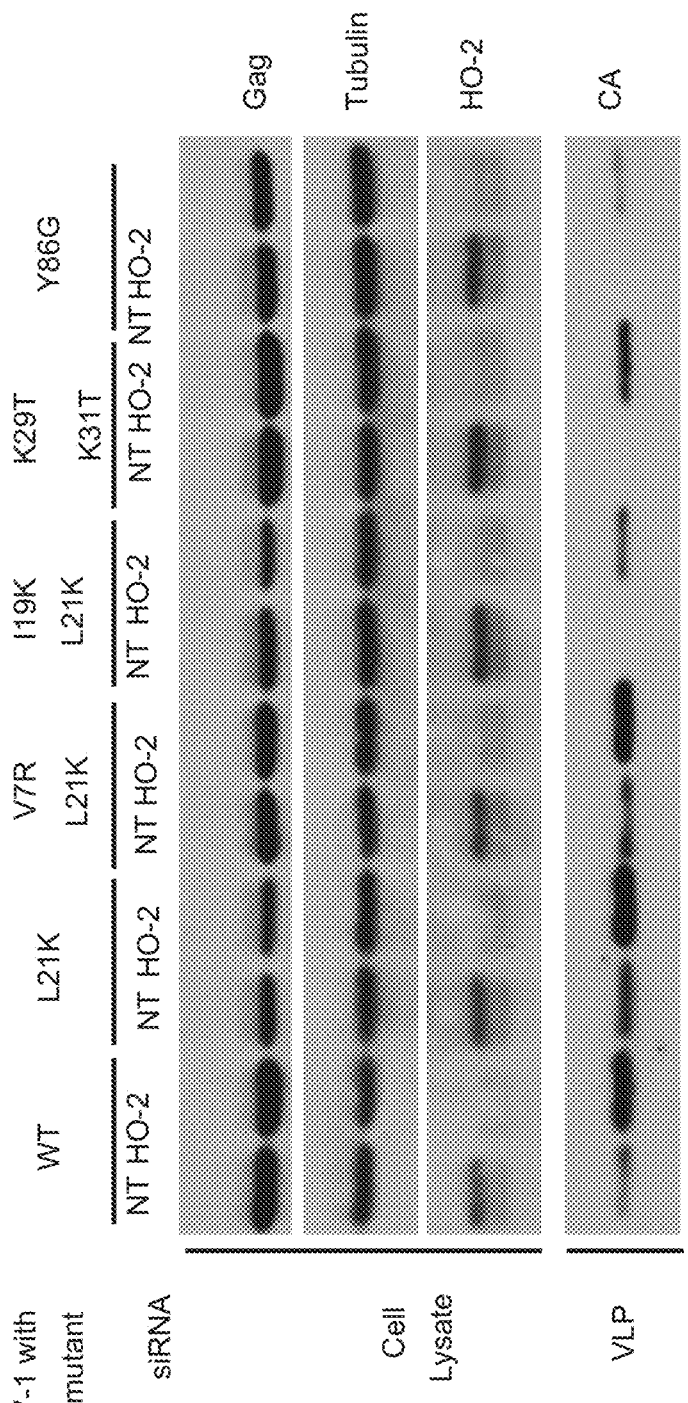
Figure 10B:
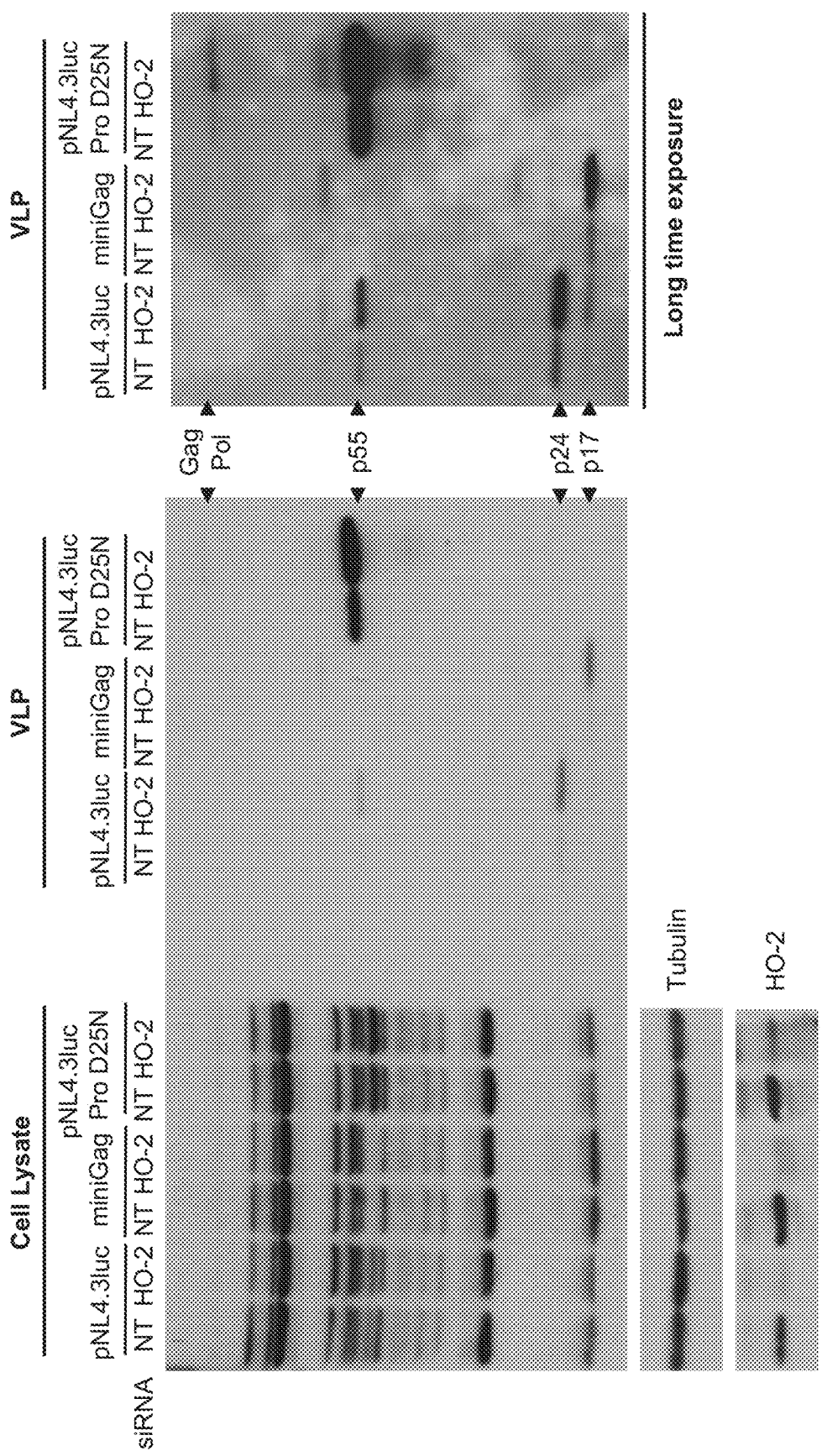

FIGS. 10A and 10B are Western blot diagrams that show that HO-2 knockdown resulted in a similar increase of HIV-1 virus production for viruses with certain MA mutations.

Figure 11:
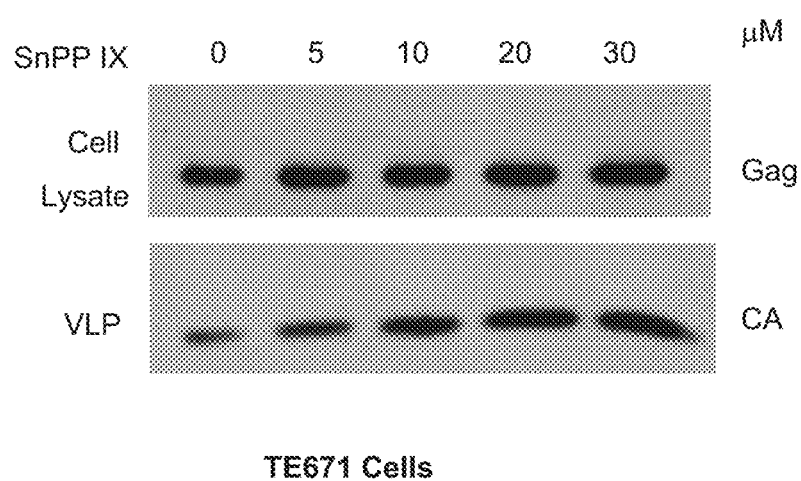

FIG. 11 is a Western blot diagram that shows increases in virus yield were observed in TE671 cells.

Figure 12A:
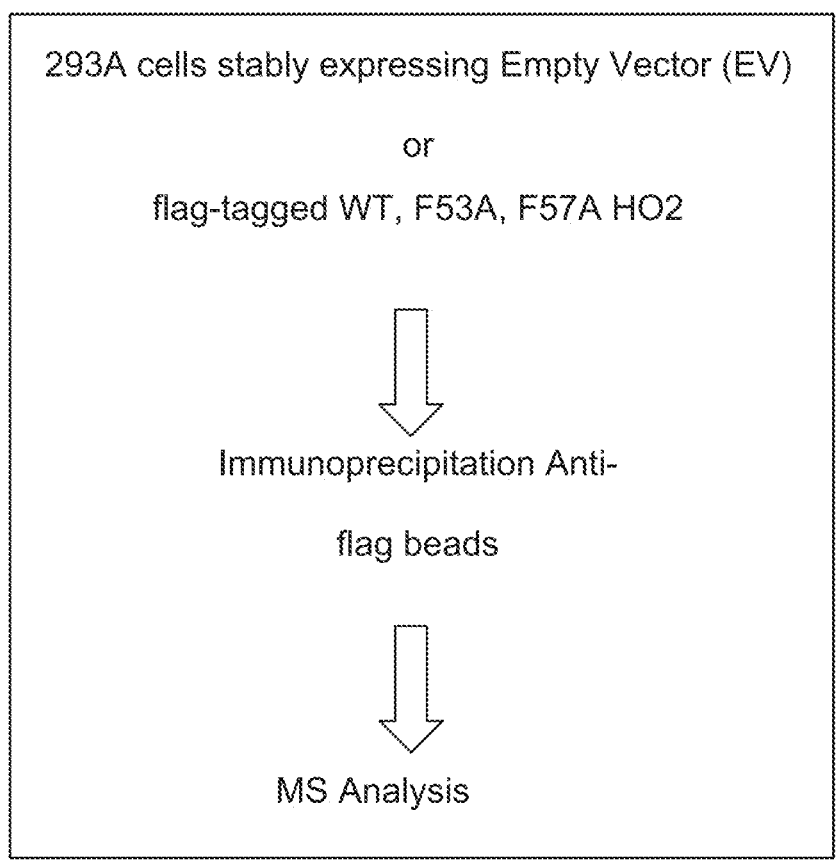

FIG. 12A is a flow diagram for the testing process and FIG. 12B is a table of the results that are obtained from the testing.

DETAILED DESCRIPTION OF THE INVENTION

For clarity, the following definitions are utilized in this document.

Group-specific antigen, the genetic material that codes for the core structural proteins of a retrovirus, is abbreviated as Gag.

Heme Oxygenase Isoenzyme 1 is abbreviated as HO-1.
Heme Oxygenase Isoenzyme 2 is abbreviated as HO-2.
Matrix domain is abbreviated as MA.
N-myristoyltransferase is abbreviated as NMT.

In an effort to find new agents that are involved in the regulation of myristoyated substrates, the inventors identified HO-2 as a protein that binds and modulates myristoylated HIV-1 Gag (Maines, 1988).

Both HO-1 and HO-2 catalyze the metabolism of heme to form biliverdin, which is subsequently converted to bilirubin and carbon monoxide. The structures of HO-1 and HO-2 have been determined, and the site for binding and cleavage of heme has been located (Bianchetti et al., 2007; Lad et al., 2003a; Schuller et al., 1999). HO-2 is constitutively expressed in all tissues and cell types, while HO-1 is also ubiquitously expressed in most normal cells but induced to very high levels upon oxidative stress, such as treatment with heme or other inflammatory stimuli (Bellner et al., 2009; Prawan et al., 2005). There have long been suggestions that HO-2 plays a role in inhibition of inflammatory responses (Seta et al., 2006). HO-2 knockout mice display higher inflammatory cytokine levels and deficiency in wound healing (Bellner et al., 2009). Overexpression of HO-2 inhibits, while RNAi-mediated depletion of HO-2 enhances, the lipopolysaccharide (LPS)-induced inflammatory response in mouse cerebral vascular endothelial cells (Chen et al., 2014).

HO-2 is shown herein to be a myristate-binding protein. The co-crystal structure at 1.9 Å resolution of HO-2 in complex with myristate reveals that HO-2 binds myristate via a long hydrophobic channel and that heme analogues block myristate binding to HO-2. The finding that HO-2 binds to N-terminal acyl groups on a large number of viral and cellular proteins is unexpected, and as noted it negatively regulates their functions. The invention further shows that LPS induces the expression of HO-2, suggesting that HO-2 is involved in the LPS-TLR4 pathway as a negative feedback regulator. This establishes that HO-2 traps myristoylated or other acylated (i.e., of C12 to C22 fatty acid) proteins to inhibit their membrane association, and hence negatively regulate their functions. Therefore, HO-2 has been found to be part of a homoeostatic negative feedback loop in cytokine induction.

As an example, it was found that HO-2 negatively regulates the membrane association of HIV-1 Gag. Accordingly, genetic knockdown of HO-2 or inhibition of HO-2's myristate-binding activity, either by mutations altering the hydrophobic channel or by addition of a noncleavable heme analogue, results in a significant increase in HIV-1 virion production. It has also been found that HO-2 also binds to TRAM, the adaptor protein of TLR4, and inhibits the TRAM-dependent LPS-TLR4-induced immune response.

Generally, therefore, a workflow of events starts with the preparation of a suitable siRNA or the construction of an shRNA expression plasmid, usually followed by the transfection of these constructs into cultured cells. mRNA and protein analyses, as well as functional assays, can be used to verify the effect of RNAi in establishing the genetic knockdown. The production of lentiviral vectors is also summarized in a chapter of a textbook authored by Rodrigues, A. et al. (2011) entitled "Production of Retroviral and Lentiviral Gene Therapy Vectors: Challenges in the Manufacturing of Lipid Enveloped Virus, Viral Gene Therapy," Dr. Ke Xu (Ed.), InTech, DOI: 10.5772/18615 and in an article by G.

Tiscornial et al. entitled "Production and Purification of Lentiviral Vectors," Nature Protocols 1, 241-245 (2006).

Accordingly, the invention now provides a new method of increasing the production of lentivirus via the new mechanism of action disclosed herein. By identifying new genetic and pharmaceutical inhibitory pathways, this technology significantly increases viral yield at a low-cost, promising to enhance the commercial utilities of lentivirus across multiple disciplines. As noted herein, this is achieved by either deletion or knockout of HO-2 in the producer cells or by adding a HO-2 myristate binding inhibitor to the producer cells.

The present invention now has identified a number of unexpected findings, including that:

HO-2 binds myristate via a hydrophobic channel
HO-2 negatively regulates the functions of myristoylated proteins
HO-2 inhibits the production of HIV-1 virions
HO-2 is a negative feedback regulator of TLR4 signaling These findings are directly applicable to improve or enhance the production of lentiviruses as they now teach that the negative effects of HO-2 on acetylated proteins can be offset by inhibiting or reducing the ability of HO-2 to bind to the acylated proteins. These findings and procedures for offsetting the effects of such HO-2 binding are now illustrated by the following Examples and test results.

Experimental Procedures

DNA Constructs pQCXIP-FH was constructed by inserting a XhoI restriction site, the flag-tag sequence, and the HA tag sequences into pQCXIP (Clontech) between BamHI and EcoRI restriction sites. cDNAs encoding the wild-type and G2A mutants of HIV-1 MA (MA), MLV MA (MMA), vSrc, and TRAM were cloned into pQCXIP-FH to construct pQCXIP-MA-FH, pQCXIP-MAG2A-FH, pQCXIP-MMA-FH, pQCXIP-MMAG2A-FH, pQCXIP-vSrc-FH, pQCXIP-vSrcG2A-FH, pQCXIP-TRAM-FH, pQCXIP-TRAMG2A-FH, respectively. The cDNA encoding human HO-2 was cloned into pCMV-Myc (Clontech) to form pCMV-Myc-HO-2. To express mutant HO-2, HO-2 CDS with each mutation (H45A, F53A, F57A, L74A, Y134A, R156A, N230A, I233A, F234A, and V54MA70V) were also cloned into pCMV-Myc vector. Plasmids pQCXIP-HO-2iR, pQCXIP-HO-2iR-H45A, pQCXIP-HO-2iR-F53A, pQCXIN-HO-2iR, pQCXIN-HO-2iR-H45A, and pQCXIN-HO-2iR-F53A were used to express wild-type HO-2 and mutant versions of HO-2 designed to be resistant to siRNA knockdown and CRIPSR knockout. Silent mutations were introduced into all four siRNA targets in HO-2 cDNA (the CRISPR target overlaps with the first siRNA target) and the cDNAs were cloned into pQCXIP and pQCXIN vectors (Clontech).

pLKO-SCR, which expresses a scrambled shRNA, was a gift from Sheila Stewart (Addgene plasmid #17920) (Saharia et al., 2008). pLKO-HO-2i253 (TRCN0000045253) and pLKO-HO-2i257 (TRCN0000045257), which express two different shRNAs targeting HO-2, were purchase from Sigma. pLentiCRISPR was a gift from Feng Zhang (Addgene plasmid #52961) (Sanjana et al., 2014). pLentiCRISPR-HO-2, which expresses the CRISPR RNA targeting HO-2, was constructed by insertion of the oligo (GACCAAGGAAGCACACGACC) into pLentiCRISPR.

The following reagent was obtained through the NIH AIDS Reagent Program, Division of AIDS, NIAID, NIH: pNL4-3.Luc from Dr. Nathaniel Landau (He et al., 1995). For HIV-1 vectors expressing Gag with different MA mutations (L21K, V7RL21K, I19KL21K, K29TK31T, Y86G) and nonfunctional proteinase (Pro D25N), the corresponding mutations were introduced into pNL4.3luc by overlap PCR. Plasmid Δ-Zwr, which expresses miniGag (an HIV-1 Gag mutant lacking most of MA and a portion of CA, but retaining the N-terminal myristoylation), was a gift from Dr. Heinrich G. Gottlinger (Accola et al., 2000). pCMV-RSV-Gag was a gift from Dr. Leslie J. Parent (Penn State College of Medicine; Hershey, Pa. USA). Plasmids used for lentivirus and retrovirus packaging, including pVSVG (expressing envelope protein VSV G), pCMVdeltaR8.2 (expressing HIV-1 Gag and GagPol), and pHIT60 (expressing MLV Gag and GagPol), have been described before (Soneoka et al., 1995).

pRANTES-Luc, which expresses firefly luciferase reporter under the promoter of human RANTES, has been described before (Fitzgerald et al., 2003). pRL-TK was obtained from Promega. pEF-Bos-TRAM-Flag (Addgene plasmid#41551) was used to express TRAM with flag tag at its C-terminal.

Cell Culture 293A (Invitrogen), HEK293T, TE671 were maintained in Dulbecco's Modified Eagle Medium plus 10% fetal bovine serum. Jurkat TAg (JTAg) cells were generously provided by Dr. Massimo Pizzato (University of Trento, Italy) and cultured in RPMI-1640 medium with 10% FBS. THP-1-MD2-CD14 cells (Invivogen, thpx-mdcdsp) were cultured in RPMI-1640 medium with 10% heat-inactivated FBS, 100 mg/ml of Normocin (Invivogen), Pen-Strep (100 U/ml), 200 µg/ml of Zeocin and 250 µg/ml of G418.

293A-FH, 293A-MA-FH, 293A-MAG2A-FH, 293A-MMA-FH, 293A-MMAG2A-FH, 293A-vSrc-FH, 293A-vSrcG2A-FH, 293A-TRAM-FH, 293A-TRAMG2A-FH, 293A-HO-2iR, 293A-HO-2iR-F53A, 293A-flagHO-2, 293A-flagHO-2-F53A, and 293A-flagHO-2-F57A stable cell lines were constructed by infecting 293A cells with VSVG pseudotyped retroviral vector pQCXIP bearing corresponding genes. Infected cells were selected and pooled in medium with 1 µg/ml puromycin.

JTag-SCR, JTag-HO-2i253, JTag-HO-2i257, THP-1-MD2-CD14-SCR, THP-1-MD2-CD14-HO-2i253, THP-1-MD2-CD14-HO-2i257, which stably express scrambled shRNA (SCR) or two different shRNAs against HO-2 (HO-2i253, HO-2i257), were constructed by infecting JTag cells or THP-1-MD2-CD14 cells with VSV-G pseudotyped pLKO-SCR, pLKO-HO-2i253, pLKO-HO-2i257 viruses, and infected cells were selected and pooled in medium with 1 µg/ml puromycin.

To knock out HO-2 expression, 293A cells were transfected with pLentiCRISPR-HO-2 and selected in medium with 1 µg/ml puromycin. Single clones were picked up and the expression of HO-2 in each clone were examined by Western blot using HO-2 antibody. Two clones (293A-HO-2KO#1, 293A-HO-2KO#6) with complete HO-2 knock out were selected and expanded for further experiments. Meanwhile, 293A cells were transfected with pLentiCRISPR. Transfected cells were selected and pooled in medium with 1 µg/ml puromycin to construct 293A-Control cells, which serve as a control cell line in the experiments with HO-2 KO cells. 293A-HO-2KO#6-FH, 293A-HO-2KO#6-HO-2, 293A-HO-2KO#6-HO-2-F53A, 293A-HO-2KO#6-HO-2-H45A cells, which stable express empty vector (FH), wild type HO-2 (HO-2), or mutant HO-2 (F53A, H45A), were constructed by infecting 293A-HO-2KO#6 cells with VSVG pseudotyped retroviral vector pQCXIN expressing corresponding version of HO-2 with silent mutations in the CRISPR target sequence. Infected cells were selected and pooled in medium with 400 µg/ml G418.

Transfection, Virus Package, and Infection

All the plasmid transfections in adherent cells were performed using lipofectamine 2000 (Invitrogen) following the manufacturer's protocol, while DMRIE-C Transfection Reagent (Invitrogen) was used for transfections in Jurkat cells.

To package VSV-G pseudotyped NL4-3luc viruses, viral vectors (pNL4-3luc) together with pVSV-G, were transfected into HEK293T cells. To package retroviral vector based VSV-G pseudotyped viruses, viral vectors together with pHIT60 (expressing MLV Gag and Gag-Pol) and pVSV-G were transfected into HEK293T cells. To package lentiviral vector based VSV-G pseudotyped viruses, viral vectors together with pCMVdeltaR8.2 (expressing HIV-1 Gag and Gag-Pol) and pVSV-G were transfected into HEK293T cells. 48 hours after transfection, mediums were filtered through 45 mm membrane to collect virus.

Unless otherwise indicated, viruses were 3-fold diluted with cell culture medium containing 20 mM HEPES (pH7.5) and 4 mg/ml polybrene. Adherent cells were infected by diluted viruses for 3 hours, while suspension cells were infected by diluted viruses overnight.

Virus-Like Particle (VLP) Detection

The supernatant medium from cells (3 ml) was layered above 1 ml of 25% sucrose in TEN buffer [10 mM Tris-Cl (pH 8.0), 0.1M NaCl, 1 mM EDTA (pH 8.0)]. Samples were centrifuged at 100,000×g (~28,000 rpm) for 2 h at 4° C. (SW55 rotor, Beckman). The virus like particle pellets were resuspended in 100 ml of 1×SDS loading buffer, resolved by SDS-PAGE, and analyzed by Western blot.

Immunoprecipitation and Western Blot

Cells were lysed in CelLytic M Cell Lysis Reagent (Sigma, C2978) for 10 min. The lysate was clarified by centrifugation at 4° C. for 15 min at 12000 rpm. The supernatant was mixed with ANTI-FLAG M2 Affinity Gel (Sigma, A2220) and the mixture was incubated at 4° C. for 4 h. The resin was washed with TBST (TBST) four times and the proteins bound to the resin were recovered and resolved by SDS-PAGE electrophoresis, transferred to a PVDF membrane and probed by Western blotting. Antibodies used in Western Blot were: Flag (Sigma, F1804); Myc (Santa Cruz, sc-40); HO-2 (Origene, TA503925); HO-1 (Origene, TA300823): RRS (Abcam, ab31537); HIV-1 p24 (Abcam, ab9701): Tubulin (Sigma, T6199); Anti-HIV1 p55+p24+p17 antibody (ab63917); ATP1A1 (Abcam, ab76020); GAPDH (Abcam, ab8245): MLV CA (homemade): RSV Gag (generously provided by Dr. Leslie J. Parent, Penn State College of Medicine; Hershey, Pa. USA).

Reagents

Reagents used included: myristic acid (Sigma, 70079); PMA (Sigma, P8139); Tin Protoporphyrin IX dichloride (Santa Cruz, sc-203452); LPS (Enzo Life Sciences, ALX-581-007-L001).

Protein Expression and Purification.

The HO-2 gene fragment encoding amino acid residues 30-242 was cloned into a pET28a vector with a 6-His tag at the N terminus without protease cleavage site. The protein was overexpressed in *Escherichia coli* BL21 (DE3) Star strain (Novagen). The cells were induced with 0.4 mM isopropyl β-D-1-thiogalactopyranoside for 12 h at 24° C. The harvested cells were resuspended in lysis buffer containing 50 mM phosphate (pH 7.6), 500 mM NaCl, 5% (v/v) glycerol, 20 mM imidazole and lysed by sonication. Cell lysates were centrifuged for 30 min at 4° C. before incubating with nickel beads (Qiagen). After 30 min, beads were transferred to a gravity flow column (Bio-Rad) and washed extensively with lysis buffer. Protein was eluted with a buffer containing 50 mM phosphate (pH 7.6), 500 mM NaCl, 5% (v/v) glycerol and 500 mM imidazole. Protein eluate was further purified by gel filtration using Sephacryl S-300 column (GE Healthcare) equilibrated in a buffer containing 5 mM HEPES (pH 7.6) and 250 mM NaCl. The protein sample were concentrated to 50 mg/ml and stored at −80° C.

Protein Crystallization.

Crystals of apo HO-2 were grown by mixing 1.2 μL protein solution (20 mg/ml) with 1.2 μL well solution (0.1 M Bis-Tris, (pH 6.5), 24% (w/v) polyethylene glycol 2,000 monomethyl ether) using hanging drop method at 20° C. Crystals appeared the following day and were transferred to the well solution with 35% (w/v) of the precipitant as cryo-protectant before being flash-frozen in liquid nitrogen.

To make the myristate complex, sodium myristate was dissolved in water at 50° C., and mixed with 20 mg/ml protein solution and incubated at 37° C. water bath for 30 min. The complex solution was then used to set up crystallization by mixing with (0.1 M Bis-Tris, (pH 5.5), 28% (w/v) polyethylene glycol 550 monomethyl ether, and 5 mM MgCl$_2$). Crystals were directly flash-frozen in liquid nitrogen.

The laurate complex crystals were obtained by soaking apo crystals in well solution with 5 mM sodium laurate overnight and transferred to well solution with 35% (w/v) of precipitant before flash-frozen in liquid nitrogen. The crystals belong to space group P2$_1$2$_1$2$_1$ and there are four protein molecules in the asymmetric unit.

Data Collection, Structure Determination and Refinement.

X-ray diffraction data sets were collected at beamline 24-ID-E of the Advanced Photon Source (APS). The data were processed with the HKL package (Otwinowski and Minor, 1997). The structures were solved by molecular replacement using entry 2Q32 from the Protein Data Bank as the model. The myristate and laurate were manually added with Coot (Emsley and Cowtan, 2004) and refined with Phenix (Adams et al., 2002). The crystallographic information is summarized in Table 1.

TABLE 1

Summary of crystallographic statistics

| Structure | Free | Myristate complex | Laurate complex |
|---|---|---|---|
| Space group | P2$_1$2$_1$2$_1$ | P2$_1$2$_1$2$_1$ | P2$_1$2$_1$2$_1$ |
| Cell dimensions | | | |
| a, b, c (Å) | 77.3, 84.3, 139.7 | 77.7, 82.9, 137.0 | 77.4, 83.9, 138.3 |
| α, β, γ (°) | 90, 90, 90 | 90, 90, 90 | 90, 90, 90 |
| Wavelength (Å) | 0.9792 | 0.9792 | 0.9792 |

TABLE 1-continued

Summary of crystallographic statistics

| Structure | Free | Myristate complex | Laurate complex |
|---|---|---|---|
| Resolution range (Å)[a] | 25-2.0 (2.07-2.0) | 25-1.9 (1.97-1.9) | 25-2.1 (2.18-2.1) |
| Unique reflections | 65,740 | 68,092 | 51,449 |
| Redundancy | 3.6 (3.6) | 3.6 (3.6) | 3.8 (3.5) |
| I/σI | 13.0 (2.3) | 17.9 (2.3) | 15.2 (2.7) |
| Completeness (%) | 99.8 (100) | 97.3 (91.6) | 99.4 (99.2) |
| $R_{merge}$ | 0.072 (0.492) | 0.058 (0.534) | 0.065 (0.385) |
| Structure refinement | | | |
| Resolution range (Å) | 25-2.0 (2.06-2.0) | 25-1.9 (1.93-1.9) | 25-2.1 (2.19-2.1) |
| No. reflections | 62,506 | 68,033 | 52,395 |
| No. atoms | 7,601 | 7,571 | 7,371 |
| $R_{work}$ | 0.198 (0.268) | 0.192 (0.266) | 0.195 (0.253) |
| $R_{free}$[b] | 0.251 (0.284) | 0.244 (0.314) | 0.249 (0.333) |
| rms deviation in bond length (Å) | 0.007 | 0.008 | 0.007 |
| rms deviation in bond angles (°) | 0.74 | 0.86 | 0.80 |
| Ramachandran analysis | | | |
| favoured (%) | 97.83 | 98.56 | 97.83 |
| Allowed (%) | 2.17 | 1.44 | 2.17 |
| outlier (%) | 0 | 0 | 0 |

[a]The values for the data in the highest resolution shell are shown in parentheses.
[b]$R_{free}$ is the same as $R_{work}$, but calculated on the 5% reflections not used in refinement siRNA Transfection Non targeting control siRNA (siNT: Catalog No. D-001810-10-20), siRNA against HO-2 (siHO-2: Catalog No. L-009630-00-0005) and siRNA against HO-1 (siHO-1: Catalog No. L-006372-00-0005) were obtained from Dharmacon. For siRNA transfection, $10^5$ 293A cells were seeded in 6-well plates. 24 hours later, siRNA were transfected into cells by Lipofectamine RNAiMax (Invitrogen) according to the manufacturer's protocol. After another 24 hours, the same siRNA transfection was performed for the second time. On the third day, the siRNA transfected cells were transfected by DNA or infected with virus for further experiments.

Luciferase Assay

Firefly luciferase activities were measured by Luciferase Assay System (Promega). *Renilla* and firefly luciferase activities were measured by the Dual-luciferase Reporter Assay System (Promega).

Membrane Floatation Assay

Membrane floatation assays were performed as described before (Sabo et al., 2011). Briefly, $5*10^6$ cells were washed twice with washing buffer [10 mM Tris-HCl (pH 7.5), 1 mM EDTA and 1 mM EGTA], suspended in 1 ml of homogenization buffer [10 mM Tris-HCl (pH 7.5), 1 mM EDTA, 10% sucrose, supplemented with protease inhibitor cocktail] and incubated on ice for 10 min. Cell suspensions were subjected to 30 strokes in a Dounce homogenizer and clarified by centrifugation at 500×g for 5 min at 4° C. After homogenization, cell extracts were adjusted to 73% sucrose by mixing 250 μl of the postnuclear supernatants with 1.25 ml of 85.5% sucrose in TE buffer [10 mM Tris pH 8.0, 1 mM EDTA] and placed at the bottom of a 12-ml ultracentrifuge tube. A discontinuous gradient was formed above the cell extracts by adding 7 ml of 65% sucrose in TE and 3 ml of 10% sucrose in TE. Samples were centrifuged at 100,000×g (~25,000 rpm) for 18 h at 4° C. (SW41 rotor, Beckman). Fractions (1.2 ml) were collected from the top of the gradient. The total proteins of each fraction were precipitated with TCA, resolved by SDS-PAGE, and analyzed by Western blot.

Cell Fractionation

Cell fractionation was performed by using Plasma Membrane Protein Extraction Kit (Abcam, ab65400).

Elisa Assay

The levels of RANTES in the supernatant of culture cells were measured by Human CCL5 (RANTES) ELISA Kit (Biolegend, 440807) according to the manufacturer's protocol.

Real-Time PCR

The mRNA levels of hZAP, RIG-I and GAPDH were measured by SYBR Green real time PCR in Rotor-gene 6000 (Corbett Life Science) using the following PCR cycle program: 1) 50° C. 2 min, 1 cycle; 2) 95° C. 10 min, 1 cycle; 3) 95° C. 15 s→60° C. 30 s→72° C. 30 s, 40 cycles; 4) 72° C. 10 min, 1 cycle. The sequences of the primers are: qHO-2 (AGAACGAGCCGGAGCTACT, CCTCCACGATC-CTCTCTTGG); qGAPDH (ATGGGGAAGGT-GAAGGTCG, GGGGTCATTGATGGCAACAATA).

EXAMPLES

In the following examples, all experimental procedures used here are standard molecular biology methods that are known and understood by persons of ordinary skill in the art. For additional details, the Appendix provides Supplemental Information.

Example 1: Knockdown of HO-2 Enhances Production of HIV-1 Virus 293A cells are first transfected with siRNAs targeting HO-2, or scrambled siRNA controls, and then transfected with DNAs encoding the VSV-G protein, and an HIV-1 based vector expressing Gag-Pol and the luciferase marker. Culture supernatants were collected after 48 h and used to infect naïve 293A cells, and the yield of infectious virus present in the harvests was determined by luciferase assays of lysates of the infected cells. Remarkably, the cells depleted of HO-2 showed an approximately seven-fold increase in the yield of infectious virus over the control cells treated with nontargeting siRNAs (FIG. 3B).

To test whether the increase in yield of infectious virus was due to an increase in the levels of virion particles produced, or to an increase in the specific infectivity of the virus, the levels of viral Gag protein in the viral harvests were assessed by Western blot. Cells were subjected to siRNA-mediated knockdown targeting either HO-1 or HO-2, transfected with viral DNAs as before, and 48 h post transfection, culture supernatants were collected and cell lysates were prepared. Virion particles were pelleted through sucrose cushions, and the levels of Gag proteins in the virions and in the cell lysates were assessed by Western blot (FIG. 3C). Cells depleted of HO-2 showed a dramatic increase in the levels of CA protein in the culture supernatant as compared to control cells, comparable to the increase in yield of infectious virus. Cells depleted of HO-1 showed no change in CA levels from the control. The knockdowns had no effect on the levels of Pr55$^{gag}$ precursor protein in the cell lysates. Probing for the levels of HO-2 and HO-1 confirmed that the knockdowns were efficient, and specific to the targeted gene product (FIG. 3C). This demonstrates that knockdown of HO-2 specifically increases the production of virion particles based on CA protein and virus infectivity assays.

To confirm that the increased HIV-1 virus production was attributable to the knockdown of HO-2 and not to off-target effects, an RNAi-resistant version of HO-2 was expressed in the knockdown cells and again the yield of virus produced after transfection with viral DNAs was measured (FIG. 3D). Re-expression of HO-2 reversed the increase in virion particle yield back to normal levels produced by control cells. Expression of a non-binding mutant of HO-2 (F53A) did not change the increased virion yield of the knockdown cells, indicating that HO-2's ability to limit virus production is dependent on its myristate-binding activity. Even though the levels of HO-2 expression in these experiments were much higher than the endogenous levels of HO-2, in no case were the levels of CA reduced below the levels seen in wild-type cells. This demonstrates that depletion of HO-2 allows for abnormally high levels of virion production, while the endogenous levels or overexpressed levels of HO-2 repress production equally to a similar basal level in unmanipulated cells.

The effect of HO-2 on virus yield was tested in several other settings. Knockdown of HO-2 in the Jurkat T cell line expressing either of two short hairpin RNAs again resulted in large increases in the yield of HIV-1 virion particles as assessed by levels of CA protein (FIG. 3E). The effect was not limited to HIV-1. Knockdown of HO-2 in 293A cells resulted in a significant increase in the levels of MLV virions produced after transfection with a DNA expressing the MLV Gag-Pol protein (FIG. 3F). Knockdown of HO-2 in 293A cells had no effect, however, on the yield of virions of the avian Rous sarcoma virus, which encodes a Gag precursor that does not include an N-terminal myristate (FIG. 3G).

The association of HIV-1 Gag with the plasma membrane and subsequent virus production is dependent on both the N-terminal myristoylation of Gag and also a cluster of basic amino acids near the amino-terminal region of MA (Hill et al., 1996; Resh, 2004). Mutation of certain residues of MA (I19K/L21K, K29T/K31 T, and Y86G) can inhibit membrane association, or can redirect HIV-1 Gag to endogenous membranes (Ono et al., 2000). These sequences of MA, however, are not absolutely required for virus production, and a mutant HIV-1 Gag lacking nearly all of MA but retaining only the first 7 amino acids (miniGag) can still support virus production (Accola et al., 2000).

To test whether portions of MA are involved in HO-2's effect on HIV-1 virus production, HO-2 was knocked down and the production of virus bearing MA mutations or deletion were examined. It was found that HO-2 knockdown resulted in a similar increase of HIV-1 virus production for virus with any of several MA mutations (FIG. 10A) or a large MA deletion (FIG. 10B, miniGag). In some cases the knockdown of HO-2 increased the virus production from nearly undetectable to readily detectable levels (FIG. 10A, B). The increase in HIV-1 virus production was not dependent on virus maturation, as virus with a mutation in the PR protease that blocked cleavage of the Pr55gag precursor still showed increased virion production upon HO-2 knockdown (FIG. 10B, Protease mutation D25N).

FIG. 10A shows that 293A cells were transfected twice with the control non-targeting siRNA (NT) or the siRNA pool against HO-2 (siRNA HO-2) and were then transfected with pNL4.3luc (WT) or pNL4.3luc bearing indicated mutations in the MA domain. 48 hours after transfection, virus like particles (VLP) were pelleted from supernatant of cells. Gag expression in the cells (cell lysate) and CA in the VLP were detected by HIV-1 p24 antibody.

FIG. 10B shows that 293A cells were transfected twice with the control non-targeting siRNA (NT) or the siRNA pool against HO-2 (siRNA HO-2) and then transfected with pNL4.3luc, plasmid A-Zwr (expressing miniGag), pNL4.3luc with dead protease mutation (Pro D25N). 48 hours after transfection, virus like particles (VLP) were pelleted from supernatant of cells. Gag expression in the cells (cell lysate) and CA in the VLP were detected by Anti-HIV1 p55+p24+p17 antibody.

Example 2: Confirmation of HO-2 as a Myristate-Binding Protein

The Matrix domain (MA) of HIV-1 Gag protein is N-myristoylated and plays an important role in HIV-1 virus budding (Bryant and Ratner, 1990: Gottlinger et al., 1989; Pal et al., 1990). To screen for host factors that interact with HIV-1 MA, a 293A cell line (293A-MA-flag) was constructed for stably expressing myristoylated HIV-1 MA with a flag epitope at the C-terminus. Cell lysates were prepared and incubated with beads containing anti-flag antibody, and the bound proteins were eluted, resolved by SDS-PAGE, visualized by Coomassie staining, and identified by mass spectrometry analysis (FIG. 8A). The most prominent bands corresponded to the subunits of the large aminoacyl-tRNA synthetase complex, previously identified in many screens as interacting with the HIV-1 MA protein (Jager et al., 2012). The functional significance of this interaction is presently unknown.

Figure 1A:
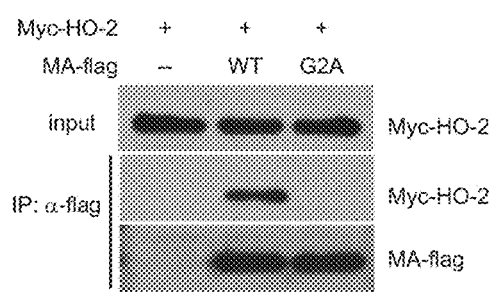
Figure 1B:
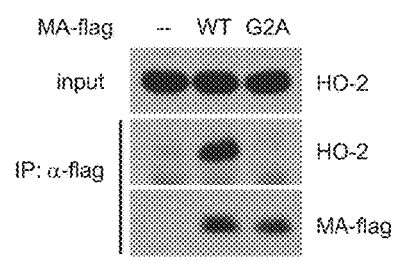

In the molecular weight range of approximately 32 kDa, HO-2 was found to be a candidate MA-interacting protein. To confirm this interaction, flag-tagged MA and myc-tagged HO-2 was coexpressed in 293A cells, lysates were prepared, the MA-flag was immunoprecipitated, and Western blots were performed to assay for bound proteins. The results in FIGS. 1A and 1B show that myc-HO-2 was efficiently bound by MA-flag, but not by an MA mutant with a substitution of the N-terminal glycine by alanine (G2A), indicating that the interaction between MA and HO-2 was strictly dependent on the N-terminal myristate (FIG. 1A). Wild-type MA also bound endogenous HO-2 (FIG. 1B), and again the G2A mutation of MA completely abolished the binding.

Figure 1C:
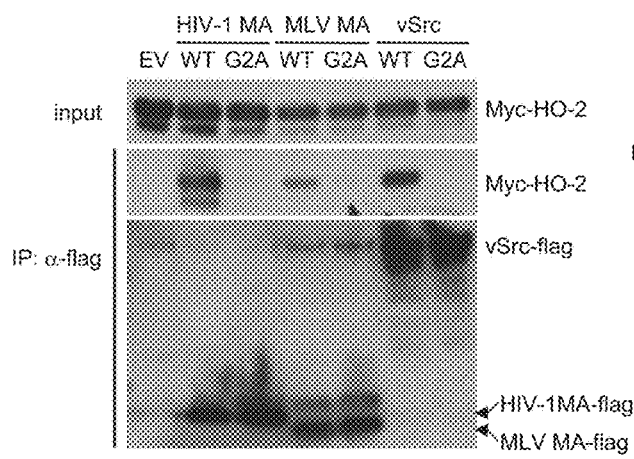
Figure 1D:
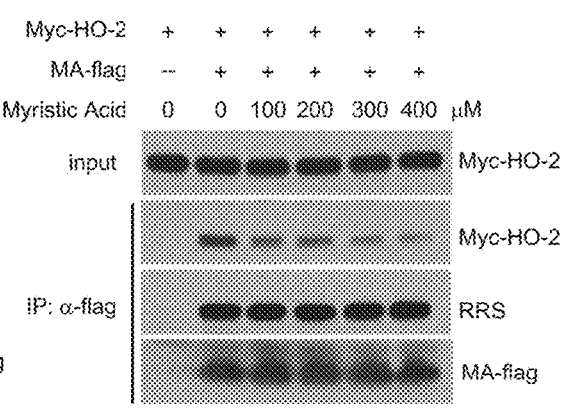

The strongly myristate-dependent interaction between HO-2 and MA suggests that HO-2 interacts with MA by binding to the N-terminal myristate directly, and thus might bind to other myristoylated or acylated proteins. The interaction between HO-2 and other proteins known to be myristoylated were then tested, including MA of Moloney leukemia virus (MLV MA) and the v-Src tyrosine kinase of Rous sarcoma virus. HO-2 bound both MLV MA and v-Src (FIG. 1C). Mutation of the N-terminal glycine of MLV MA or v-Src to prevent N-myristoylation again eliminated their interactions with HO-2 (FIG. 1C). HO-2, however, did not bind to all myristoylated proteins; a survey for binding to the Src family kinases showed strongest binding to c-Src itself, weaker binding to several kinases, and no detectable binding to others (FIG. 8B). If HO-2 is a myristate binding protein, then myristic acid or other compounds containing a myristate group (e.g. Phorbol 12-myristate 13-acetate, PMA) should block HO-2's binding to HIV-1 MA. The addition of myristic acid or PMA to the cell lysates was found to indeed decrease the interaction between HO-2 and HIV-1 MA in a dose-dependent manner (FIGS. 1D, 8C).

As a control, the interaction between MA and another MA-interacting protein, arginyl-tRNA synthetase (RRS), a subunit of the aminoacyl-tRNA synthetase complex, was also evaluated. The coimmunoprecipitation of RRS and HIV-1 MA was not affected by addition of myristic acid (FIG. 1D). These findings that HO-2 bound to many different myristoylated proteins and that free myristic acid could compete with HIV-1 MA for binding to HO-2 demonstrate that HO-2 is a myristate-binding protein.

FIG. 8A shows that the cell lysates of 293A-FH (EV) and 293A-MA-FH (MA-flag) were subjected to immunoprecipitation using anti-flag antibody beads. Proteins bound on the beads were eluted and resolved in 4%-20% gradient SDS-PAGE gel and visualized by Coomassie Staining. The bands were cut out and analyzed by Mass Spectrometry. The proteins recovered from the arrow indicating bands were shown on the right side. Numbers in the parenthesis are the peptide numbers recovered by Mass Spectrometry.

FIG. 8B shows that the interaction between HO-2 and Src family kinase. HEK293T cells were transfected with myc-tagged HO-2 and empty vector or indicated Src family kinases (SFK) with flag tag at their C-terminals. 48 hours after transfection, cell lysates were subjected to immunoprecipitation using anti-flag antibody beads. Myc-HO-2 and flag tagged Src family kinases were detected by Western blot using anti-Myc and anti-flag antibodies, respectively. SFK: Src family kinases.

FIG. 8C shows that 293A-FH (MA-flag−) or 293A-MA-FH (MA-flag+) cells were transfected with pCMV-Myc-HO-2. Cell lysates were added with indicated amount of myristic acid or PMA and then subjected to immunoprecipitation using anti-flag antibody beads. Myc-HO-2 and MA-flag were detected by Western blot using anti-Myc and anti-flag antibodies respectively, while RRS was detected by specific RRS antibody. 5% of the total cell lysate were used as input. IP: immunoprecipitation.

Example 3: Crystal Structure of Myristate-Bound HO-2

To define the molecular details of the interactions between HO-2 and myristate, the crystal structure of the complex was determined at 1.9 Å resolution (FIG. 2A; Table 1). Electron density for myristate was observed in a deep hydrophobic channel in all four molecules of HO-2 in the crystallographic asymmetric unit. The myristate has especially close contacts with the side chains of Phe53, Phe57 and Phe234 (FIGS. 2B and 2C). The myristate assumed either one of two distinct orientations in the structure. In one complex, the aliphatic chain of myristate chain is strongly bent or curved. The carboxylate group is located near a large opening of the pocket (FIG. 2B) and has very weak electron density (FIG. 2D), suggesting that it is mostly disordered, and is more accessible to solvent, providing space and flexibility in the positioning of a polypeptide attached to it by an amide bond. Thus, this structure is most likely the binding mode of myristoylated polypeptides. In the other complex, the myristate is bound in the opposite orientation, with the carboxylate more tightly ordered, deeper in the pocket, and located close to the side chains of Tyr134, Arg 156 and Asn230 (FIG. 9A, 9B, 9C). In this binding mode, the carboxylate would not be accessible to myristoylated proteins. It was observed probably because free myristate was used in these experiments.

The crystal structure was also determined at 2.1 Å resolution of human HO-2 in complex with the C12 fatty acid laurate (FIG. 2E, Table 1B). The crystal was isomorphous to that of the myristate complex. Good electron density for laurate was observed in two of the four HO-2 molecules. Laurate is positioned similarly to myristate (FIG. 2E), but the carboxylate group is ordered in the complex (FIG. 2F). In addition, the crystal structure of free HO-2 was obtained at 2.0 Å resolution (Table 1), without adding laurate or myristate during crystallization. There is no electron density in the hydrophobic pocket in this structure, confirming that the observed electron density was truly due to the laurate or myristate that was introduced during crystallization.

To assess the importance of the hydrophobic pocket residues for the myristate-binding activity of HO-2, each of selected amino acids was mutated to alanine, and the resulting interaction between the mutant HO-2 proteins and HIV-1 MA was observed by coimmunoprecipitation. While the wild type HO-2 efficiently bound HIV-1 MA, mutation of Phe53, Phe57, Phe234, or Arg 156 completely eliminated binding activity, while mutation of Leu74, Tyr134 or Ile233 reduced the binding and mutation of Asn230 also provided a small reduction on binding (FIG. 2G).

Human HO-1 is highly similar to HO-2, with 45% amino acid sequence identity (FIG. 9E) and a similar overall structure (Beale and Yeh, 1999; Lad et al., 2003a; Lad et al., 2003b; Rahman et al., 2008) and hydrophobic pocket (Bianchetti et al., 2007). Many of the residues that are important for HO-2's myristate-binding activity are also conserved in HO-1 (FIG. 9E) (Bianchetti et al., 2007). However, HO-1 does not interact with HIV-1 MA (FIG. 9F), suggesting it does not have myristate-binding activity. Superimposition of the HO-1 and HO-2 structures revealed the presence of particular residues in HO-1 (especially Met34 and Val50) that would be predicted to make the hydrophobic pocket unfavorable for myristate binding (FIG. 9G). Mutation of the corresponding residues in HO-2 (Val54 and Ala70) to those residues present in HO-1 (V54M/A70V) significantly reduced HO-2's myristate-binding activity (FIG. 2G). Overall, these mutagenesis studies confirm the importance of the residues predicted by the crystal structure to contact with myristate.

FIG. 9A shows that schematic drawing of the structure of HO-2 in complex with myristate in which the position of myristate is flipped. HO-2 is shown as ribbons (gray) and myristate as sticks (sand).

FIG. 9B shows that omit $F_o$-$F_c$ electron density at 1.9 Å resolution for myristate in (A), contoured at 2.5 s.

FIG. 9C shows that molecular surface of HO-2 in the myristate binding site, colored by electrostatic potential. The carboxylate of the flipped myristate (sand) is bound deep in the hydrophobic pocket.

FIG. 9D shows that structural overlay showing detailed interactions between myristate and HO-2 with myristate in the two observed orientations. The positions of myristate are flipped around in the two different complexes. The interactions of the aliphatic portion of myristate with HO-2 are similar in both complexes, and most of the residues lining the pocket have essentially the same conformation in the two complexes. However, Asn230 (N230) assumes a different rotamer in the two complexes, and in one case would clash with the carboxylate group. This side chain may therefore function as a 'gate', regulating access to the deeper part of the pocket.

FIG. 9E shows that sequence alignment of human HO-2 and HO-1. Identical residues are highlighted in red. Black ovals indicate residues in contact with myristate that are identical in HO-2 and HO-1, while the magenta ovals indicate residues in the binding site that are different.

FIG. 9F shows that the cell lysates of 293A-FH (MA-flag−), 293A-MA-FH (MA-flag WT), or 293A-MAG2A-FH (MA-flag G2A) cells were subjected to immunoprecipitation using anti-flag antibody beads. The endogenous HO-1 was detected by specific HO-2 antibody.

FIG. 9G shows that overlay of the structures of human HO-2 (light cyan) and HO-1 (salmon) near the myristate (black) binding site.

Example 4: Heme Analogue Binding Blocks HO-2's Myristate-Binding Activity

The two heme oxygenases in mammalian cells bind and cleave heme to form biliverdin. Superposition of the structure of heme-bound HO-2 with myristate-bound HO-2 revealed that the heme binding site is close to the opening of the hydrophobic pocket of HO-2 and suggests that heme binding could block the access of myristate to the pocket (FIG. 4A). To test this possibility, a noncleavable heme analogue was tested. Metal-protoporphyrin IX chelates, such as tin protoporphyrin IX dichloride (SnPPIX), bind to the heme oxygenases and inhibit their activity by competing with heme for binding to the enzymes but are not themselves cleaved (Drummond and Kappas, 1981). HIV-1 MA was expressed in 293A cells, lysates were prepared and tested for the coimmunoprecipitation of endogenous HO-2 with MA in the presence of increasing concentrations of SnPPIX (FIG. 4B). The addition of SnPPIX strongly inhibited the interaction between HIV-1 MA and HO-2 in a dose-dependent manner (FIG. 4B). SnPPIX had no effect on the interaction between HIV-1 MA and another MA-binding protein, the arginyl tRNA synthetase (RRS), whose interaction with MA is independent of its N-myristoylation (FIG. 4B).

To test whether SnPPIX would affect the activity of HO-2 in modulating virion production, 293A cells were transfected with viral DNA and incubated with increasing concentrations of SnPPIX. Virions were collected from culture supernatants and the CA levels were assessed by Western blot. The addition of SnPPIX in the range of 20-40 micromolar concentrations caused dramatic increases in virus yield, comparable to those seen after knockdown of HO-2 (FIG. 4C). Similar increases in virus yield were observed in TE671 cells (FIG. 11). These observations indicate that binding of the heme analogue blocked the myristate-binding activity of HO-2 and prevented HO-2's normal inhibition of HIV-1 virion production. FIG. 11 shows that TE671 cells were then transfected with pNL4.3luc and then treated with SnPP IX at indicated concentrations for 48 hours. Virus like particles (VLP) were pelleted from supernatant of cells. Gag expression in the cells (cell lysate) and CA in the VLP were detected by HIV-1 p24 antibody.

Example 5: The Myristate-Binding Activity of HO-2 Negatively Regulates the Membrane Association of HIV-1 Gag HIV-1 Gag is normally translated in the cytoplasm as a soluble protein, but then is rapidly transported to the plasma membrane to initiate virion assembly. The insertion into the membrane can be assayed by monitoring the fraction of the Gag protein in cell lysates that floats upward to low density through a sucrose overlayer upon ultracentrifugation. To test for the potential role of HO-2 in regulating the membrane association of Gag, we examined the fraction of the intracellular Gag protein that was associated with membrane after manipulating the levels of HO-2. Cells expressing Gag were lysed under mild conditions, the membrane-associated proteins were fractionated by floatation during centrifugation, and the Gag protein was assessed by Western blot. These assays showed that less than 10% of the Gag protein was associated with membrane in 293A cells (FIG. 5A), but knockdown of HO-2 by siRNA significantly increased the level of Gag in the membrane fraction (FIG. 5A).

Overexpression of wild type HO-2 (HO-2 WT) reduced the portion of membrane associated Gag back to a level comparable to that seen in control 293A cells transfected with non-targeting siRNAs (FIG. 5B). Overexpression of mutant HO-2 deficient in myristate-binding activity (HO-2 F53A) did not reduce the levels of membrane-associated Gag protein. These results indicate that the binding of HO-2 to the N-terminal myristate moiety of Gag acts to inhibit its membrane association.

Example 6: The Interaction of HO-2 with HIV-1 MA Suggests that it Plays a Role in Some Aspect of HIV-1 Replication To test for a role in the early phase of the viral life cycle, including steps of entry into the cell, reverse transcription of the genome, and integration of the viral DNA, HO-2 was depleted from 293A cells by siRNA-mediated knockdown, and the cells were then challenged by infection with the HIV-1-based vector NL4.3luc, delivered in HIV-1 virus-like particles pseudotyped by the VSV-G envelope. The knockdown of HO-2 had no measurable effect on the efficiency of transduction by these virus preparations, tested at two multiplicities of infection (FIG. 3A).

Example 7: HO-2's Myristate Binding Activity Regulates the LPS-TLR4 Signaling Pathway Via TRAM It has been estimated that ~0.5-3% of cellular proteins in mammalian cells—perhaps several hundred proteins—are modified by addition of N-terminal myristate (Martinez et al., 2008; Maurer-Stroh et al., 2002). HO-2 therefore might be able to bind and regulate the function of a large number of cellular proteins. To search for such proteins, 293A cell lines were constructed for stably expressing flag-tagged versions of either wild type HO-2 (HO-2 WT) or mutants HO-2 deficient in myristate-binding activity (HO-2 F53A or F57A), HO-2 with anti-flag antibodies were immunoprecipitated, and the bound proteins were analyzed by mass spectrometry (FIG. 12A). Among the large number of proteins binding to HO-2, 29 were identified that were preferentially associated with wild-type HO-2 but not with F53A or F57A mutants (FIG. 12B). Toll-like receptor adaptor molecule 2 (TRAM, aka TICAM2), an adaptor molecule involved in the innate immune signaling pathway downstream of the TLR4 cell surface receptor, was observed. It has been previously reported that TRAM is myristoylated and that myristoylation is essential for its function in the LPS-TLR4 immune response (Kagan et al., 2008; Rowe et al., 2006: Sacre et al., 2007). The HO-2 interaction with TRAM was confirmed by coimmunoprecipitation, and mutants were tested to show that the interaction required myristoylation of TRAM and the hydrophobic pocket of HO-2, but not the heme oxygenase activity (FIG. 6A).

TRAM activates the IRF3- and NFκB-dependent immune and inflammation response to induce the expression of the chemokine RANTES (alias C—C motif ligand 5, CCL5) (Fitzgerald et al., 2003; O'Neill et al., 2013; Yamamoto et al., 2003). The LPS-induced expression of RANTES is independent of MyD88, but specifically dependent on TRAM (Fitzgerald et al., 2003). To test for the ability of HO-2 to modulate this signaling pathway, a readout of the ability of ectopic expression of TRAM to activate RANTES expression was used. Using a luciferase gene under the control of the RANTES promoter as reporter (RANTES-luc), it was found that overexpression of TRAM by transfection of an expression construct in 293A cells induced the expression of RANTES-luc in a dose-dependent manner, with 0.8 μg of DNA inducing luciferase levels by approximately 10-fold (FIG. 6B).

Two clones of 293A cells were generated in which all copies of the HO-2 gene were knocked out by CRISPR (293A-HO-2KO #1 and #6), and the ability of TRAM to activate the reporter in these lines was tested. TRAM's ability to induce RANTEs-luc was increased from 10-fold to more than 25-fold in these KO lines (FIG. 6B). Conversely, overexpression of wild-type HO-2 in HO-2 KO 293A cells dramatically reduced TRAM's ability to induce RANTES-luc, while a mutant HO-2 deficient in myristate-binding activity (HO-2 F53A) failed to do so (FIG. 6C). Notably, a mutant HO-2 without heme oxygenase activity (HO-2 H45A) could still inhibit TRAM's function in activating RANTES-luc (FIG. 6C). These results indicate that HO-2's inhibitory effect on the function of TRAM is dependent on its myristate-binding activity, but not on its heme oxygenase activity.

To further confirm the involvement of HO-2 in the LPS-TLR4 pathway, two clones of THP-1-MD2-CD14 cells with stable knockdown of HO-2 were generated, and the induction of RANTES by increasing doses of LPS was examined. In the parental THP-1-MD2-CD14 cells, the expression of RANTES was induced by LPS at a concentration of approximately 1 ng/ml, while in THP-1-MD2-CD14 cells with HO-2 knockdown, RANTES was induced by LPS at concentrations as low as 1 μg/ml (FIG. 6D). When cells were treated with LPS at 1 ng/ml, the levels of RANTES in the supernatant of HO-2 knockdown cells were 3 to 5 fold higher than levels from control cells (FIG. 6D). Earlier observations (Barreiro et al., 2002; Litvak et al., 2009) that the expression of HO-2 can be induced by LPS were also confirmed. Treatment of THP-1-MD2-CD14 cells with 10 ng/ml LPS induced the expression of HO-2 by approximately 2.5-fold over the basal level, peaking at about 8 hours and returning to baseline after 24 hours (FIG. 6E). These results suggest that HO-2 acts as a negative feedback regulator of the LPS-TLR4 pathway by binding to the N-terminal myristate moiety and down regulating the function of TRAM.

FIG. 12A shows that flowchart of the strategy to identify host proteins that bind to wild type HO-2 (WT), but not HO-2 deficient with myristate-binding activity (F53A, F57A). FIG. 12B shows that proteins recovered by Mass Spec that that bind to wild type HO-2 (WT), but not HO-2 deficient with myristate-binding activity (F53A, F57A).

Discussion of Results of the Examples

HO-2 has been identified as a myristate-binding protein (FIG. 1) and HO-2 binding to the N-terminal myristate moiety of myristoylated proteins via a hydrophobic pocket has been demonstrated (FIG. 2A-2G). HO-2 binds both viral and cellular myristoylated proteins, including HIV-1 Gag (FIG. 1C), v-Src (FIG. 1C), and TRAM (FIG. 6A). The interaction of HO-2 with its binding partners does not seem to enhance the function of the partner, nor to promote the delivery of the partner to the membrane. Instead, endogenous HO-2 levels were found to negatively regulate the functions of targeted myristoylated proteins (FIGS. 3A-3G and FIGS. 6B-6C). HO-2, at its endogenous levels, is observed to inhibit or delay the association of its binding partners with membrane. The binding of HO-2 to the N-terminal myristate moiety of HIV-1 Gag inhibited HIV-1 virus production (FIG. 7). Binding of HO-2 to the cellular myristoylated protein TRAM inhibited the function of TRAM and down regulated the LPS-TLR4 signaling pathway (FIG. 7).

The involvement of HO-2 in the LPS-TLR4 pathway has been previously noted; overexpression of HO-2 inhibits, while knockdown of HO-2 enhances, the expression of IL-6 and TNFα induced by LPS in cerebral vascular endothelial cells (Chen et al., 2014). Without being bound by theory, the present results provide a mechanistic explanation for these observations, suggesting that HO-2 regulates the LPS-TLR4 pathway by specifically targeting the TLR4 adaptor protein TRAM (FIG. 6A-6E). LPS treatment has been shown to induce the expression of HO-2 in diaphragm and primary macrophages (Barreiro et al., 2002; Litvak et al., 2009). It was also determined that LPS treatment induced the expression of HO-2 in THP-1-MD2-CD14 cells (a monocyte cell line expressing the two TLR4 accessory proteins MD2 and CD14) (FIG. 6E). These results indicate that HO-2 acts as a negative feedback regulator in the LPS-TLR4 pathway, and are consistent with the observation that HO-2 KO mouse display higher levels of inflammatory cytokines (Bellner et al., 2009).

Many of the regulatory functions mediated by HO-2 may involve changes in the localization or trafficking of its binding partners. The myristoyl moiety of retroviral Gag proteins and TRAM protein plays a major role in their localization to the membrane, as demonstrated by the finding that mutating the first glycine to alanine (G2A) to prevent the myristoylation completely blocks their membrane association (Ono and Freed, 1999; Rowe et al., 2006). Proteins that bind myristate thus have the potential to directly and profoundly affect the membrane localization of many cellular proteins. HO-2 may trap the myristate moiety of Gag and prevent it from inserting in its proper conformation into the membrane, thereby inhibiting Gag multimerization and HIV-1 virion production (FIG. 7). Upon depletion of HO-2, myristoylated Gag is more efficiently delivered to the plasma membrane, resulting in higher yields of released virions.

Myristoylated TRAM is localized in membranes (Rowe et al., 2006) and the trafficking of TRAM from plasma membrane to the endogenous membrane is essential for its signaling function in the LPS-TLR4 pathway (Kagan et al., 2008). HO-2's inhibitory effect on TRAM could be mediated either by blocking the proper membrane association of TRAM or by interfering with the proper trafficking of TRAM between different membrane compartments. UNC119, a myristate-binding protein mainly expressed in retinal cilium (Higashide and Inana, 1999: Swanson et al., 1998), has been shown to dissociate myristoylated target proteins from membrane and facilitate their trafficking through the cytosol between different membranes (Constantine et al., 2012; Wright et al., 2011; Zhang et al., 2011). HO-2 may be acting similarly. The binding of the myristate moiety of myristoylated proteins and dissociating them from the membrane may be a common mechanism used by myristate-binding proteins to regulate the localization and function of myristoylated target proteins.

HO-2 interacts with many different myristoylated proteins (FIG. 1C), but the strength of the interaction varies widely. For example, based on the efficiency of coimmunoprecipitation, the interaction between HO-2 and MLV MA is much weaker than the interaction between HO-2 and HIV-1 MA (FIG. 1C). HO-2 binds some but not all Src family members (FIG. 8B). The structure of the myristate-HO-2 complex revealed that the myristate moiety is buried in the bottom of a hydrophobic pocket, and the carboxylate group, the site of attachment to the substrate, is very close to the protein surface (FIG. 2). Thus, when a myristoylated protein is bound by HO-2, it is likely that not only the myristate moiety, but also the N-terminal amino acids interact with HO-2. The specificity of binding of two other myristate-binding proteins, the N-myristoyl transferase (NMT) and UNC119, is controlled by interaction with both the N-terminal myristate and the first six amino acids of the myristoylated protein (Kishore et al., 1993: Zhang et al., 2011). The different N-terminal proximal sequences may similarly account for the varied interaction strengths of different myristoylated proteins with HO-2. In addition, the myristoyl moiety of many myristoylated proteins may be buried and sequestered in hydrophobic pockets and thus not available for recognition by HO-2 (Hantschel et al., 2003; Patwardhan and Resh, 2010).

Among the myristoylated proteins that are bound by HO-2, the v-Src kinase is of special interest. As early as 1990, a 32-kD plasma membrane protein was discovered to bind to the N-terminal myristate moiety of v-Src (Resh and Ling, 1990). Considering that HO-2 is a ~36 kDa membrane binding protein, and that its interaction with v-Src is dependent on the N-myristoylation, it is believed that HO-2 is the long-sought myristate binding protein for v-Src. It is as yet unknown whether HO-2 functions to regulate the kinase and transforming activities of v-Src, or the functions of the c-Src kinase family members.

It is anticipated that HO-2 binds and regulates molecules with hydrocarbon chains other than myristate. Two other proteins that bind myristate show some flexibility in the length of the acyl chains of the bound fatty acids: UNC119 can bind to laurate (12-carbon) or myristate (14-carbon) (Wright et al., 2011; Zhang et al., 2011), while NMT can bind to both myristate and palmitate (16-carbon) (Bhatnagar et al., 1994; Kishore et al., 1993). The position of myristic acid in complex with HO-2 (FIG. 2A, 2B) suggests that HO-2 could bind and regulate proteins carrying acyl chains that are somewhat longer or shorter than myristate. As it was confirmed directly that HO-2 could indeed bind to both laurate and palmitate (FIG. 2E), and the set of proteins that were identified as bound by HO-2 included several known or candidate palmitoylated proteins, including KIAA2013, MBLAC2, and SCAMP2 (Dowal et al., 2011), it is anticipated that HO-2 would bind to many acetylated proteins that include C12 to C22 fatty acid groups.

Accordingly, myristoylation of the MA of HIV-1 Gag is required for its membrane association and for virion assembly. HO-2 has been shown to specifically recognize the N-terminal myristate moiety of HIV-1 MA. A crystal structure reveals that HO-2 binds myristate via a hydrophobic channel adjacent to the heme binding pocket. It has also been found that Inhibiting HO-2 expression, or blocking myristate binding with a heme analogue, leads to large increases in HIV-1 production because HO-2 traps the myristate moiety of many myristoylated proteins and negatively regulates their functions. In particular, toll-like receptor adaptor molecule 2 (TRAM), a myristoylated adaptor protein for Toll-like receptor 4 (TLR4) is a cellular protein that binds to HO-2. Knockout of HO-2 caused hyperresponsive TRAM-dependent TLR4 signaling, and hypersensitivity to its ligand lipopolysaccharide.

REFERENCES

Accola, M. A., Strack, B., and Gottlinger, H. G. (2000). Efficient particle production by minimal Gag constructs which retain the carboxy-terminal domain of human immunodeficiency virus type 1 capsid-p2 and a late assembly domain. J Virol 74, 5395-5402.

Adams, P. D., Grosse-Kunstleve, R. W., Hung, L.-W., Ioerger, T. R., McCoy, A. J., Moriarty, N. W., Read, R. J., Sacchettini, J. C., Sauter, N. K., and Terwilliger, T. C. (2002). PHENIX: building a new software for automated crystallographic structure determination. Acta Cryst D58, 1948-1954.

Aitken, A., Cohen, P., Santikarn, S., Williams, D. H., Calder, A. G., Smith, A., and Klee, C. B. (1982). Identification of the NH2-terminal blocking group of calcineurin B as myristic acid. FEBS Lett 150, 314-318.

Barreiro, E., Comtois, A. S., Mohammed, S., Lands, L. C., and Hussain, S. N. (2002). Role of heme oxygenases in sepsis-induced diaphragmatic contractile dysfunction and oxidative stress. Am J Physiol Lung Cell Mol Physiol 283, L476-484.

Beale, S. I., and Yeh, J. I. (1999). Deconstructing heme. Nat Struct Biol 6, 903-905.

Bellner, L., Martinelli, L., Halilovic, A., Patil, K., Purl, N., Dunn, M. W., Regan, R. F., and Schwartzman, M. L. (2009). Heme oxygenase-2 deletion causes endothelial cell activation marked by oxidative stress, inflammation, and angiogenesis. J Pharmacol Exp Ther 331, 925-932.

Bhatnagar, R. S., Jackson-Machelski, E., McWherter, C. A., and Gordon, J. I. (1994). Isothermal titration calorimetric studies of *Saccharomyces cerevisiae* myristoyl-CoA:protein N-myristoyltransferase. Determinants of binding energy and catalytic discrimination among acyl-CoA and peptide ligands. J Biol Chem 269, 11045-11053.

Bianchetti, C. M., Yi, L., Ragsdale, S. W., and Phillips, G. N., Jr. (2007). Comparison of apo- and heme-bound crystal structures of a truncated human heme oxygenase-2. J Biol Chem 282, 37624-37631.

Bouamr, F., Scarlata, S., and Carter, C. (2003). Role of myristylation in HIV-1 Gag assembly. Biochemistry 42, 6408-6417.

Boutin, J. A. (1997). Myristoylation. Cell Signal 9, 15-35.

Bryant, M., and Ratner, L. (1990). Myristoylation-dependent replication and assembly of human immunodeficiency virus 1. Proc Natl Acad Sci USA 87, 523-527.

Chen, R. J., Yuan, H. H., Zhang, T. Y., Wang, Z. Z., Hu, A. K., Wu, L. L., Yang, Z. P., Mao, Y. J., Ji, D. J., and Zhu, X. R. (2014). Heme oxygenase-2 suppress TNF-alpha and IL6 expression via TLR4/MyD88-dependent signaling pathway in mouse cerebral vascular endothelial cells. Mol Neurobiol 50, 971-978.

Chung, J., Torta, F., Masai, K., Lucast, L., Czapla, H., Tanner, L. B., Narayanaswamy, P., Wenk, M. R., Nakatsu, F., and De Camilli, P. (2015). INTRACELLULAR TRANSPORT. PI4P/phosphatidylserine countertransport at ORP5- and ORP8-mediated ER-plasma membrane contacts. Science 349, 428-432.

Constantine, R., Zhang, H., Gerstner, C. D., Frederick, J. M., and Baehr, W. (2012). Uncoordinated (UNC) 119: coordinating the trafficking of myristoylated proteins. Vision Res 75, 26-32.

Cross, F. R., Garber, E. A., Pellman, D., and Hanafusa, H. (1984). A short sequence in the p60src N terminus is required for p60src myristylation and membrane association and for cell transformation. Mol Cell Biol 4, 1834-1842.

Dowal, L., Yang, W., Freeman, M. R., Steen, H., and Flaumenhaft, R. (2011). Proteomic analysis of palmitoylated platelet proteins. Blood 118, e62-73.

Drummond, G. S., and Kappas, A. (1981). Prevention of neonatal hyperbilirubinemia by tin protoporphyrin IX, a potent competitive inhibitor of heme oxidation. Proc Natl Acad Sci USA 78, 6466-6470.

Emsley, P., and Cowtan, K. D. (2004). Coot: model-building tools for molecular graphics. Acta Cryst D60, 2126-2132.

Fitzgerald, K. A., Rowe, D. C., Barnes, B. J., Caffrey, D. R., Visintin, A., Latz, E., Monks, B., Pitha, P. M., and Golenbock, D. T. (2003). LPS-TLR4 signaling to IRF-3/7 and NF-kappaB involves the toll adapters TRAM and TRIF. J Exp Med 198, 1043-1055.

Giang, D. K., and Cravatt, B. F. (1998). A second mammalian N-myristoyltransferase. J Biol Chem 273, 6595-6598.

Gottlinger, H. G., Sodroski, J. G., and Haseltine, W. A. (1989). Role of capsid precursor processing and myristoylation in morphogenesis and infectivity of human immunodeficiency virus type 1. Proc Natl Acad Sci USA 86, 5781-5785.

Hantschel, O., Nagar, B., Guettler, S., Kretzschmar, J., Dorey, K., Kuriyan, J., and Superti-Furga, G. (2003). A myristoyl/phosphotyrosine switch regulates c-Abl. Cell 112, 845-857.

He, J., Choe, S., Walker, R., Di Marzio, P., Morgan, D. O., and Landau, N. R. (1995). Human immunodeficiency virus type 1 viral protein R (Vpr) arrests cells in the G2 phase of the cell cycle by inhibiting p34cdc2 activity. Journal of virology 69, 6705-6711.

Henderson, L. E., Krutzsch, H. C., and Oroszlan, S. (1983). Myristyl amino-terminal acylation of murine retrovirus proteins: an unusual post-translational proteins modification. Proc Natl Acad Sci USA 80, 339-343.

Hermida-Matsumoto, L., and Resh, M. D. (1999). Human immunodeficiency virus type 1 protease triggers a myristoyl switch that modulates membrane binding of Pr55 (gag) and p17MA. J Virol 73, 1902-1908.

Higashide, T., and Inana, G. (1999). Characterization of the gene for HRG4 (UNC119), a novel photoreceptor synaptic protein homologous to unc-119. Genomics 57, 446-450.

Hill, C. P., Worthylake, D., Bancroft, D. P., Christensen, A. M., and Sundquist, W. I. (1996). Crystal structures of the trimeric human immunodeficiency virus type 1 matrix protein: implications for membrane association and assembly. Proc Natl Acad Sci USA 93, 3099-3104.

Jager, S., Cimermancic, P., Gulbahce, N., Johnson, J. R., McGovern, K. E., Clarke, S. C., Shales, M., Mercenne, G., Pache, L., Li, K., et al. (2012). Global landscape of HIV-human protein complexes. Nature 481, 365-370.

Kagan, J. C., Su, T., Horng, T., Chow, A., Akira, S., and Medzhitov, R. (2008). TRAM couples endocytosis of Toll-like receptor 4 to the induction of interferon-beta. Nat Immunol 9, 361-368.

Kishore, N. S., Wood, D. C., Mehta, P. P., Wade, A. C., Lu, T., Gokel, G. W., and Gordon, J. I. (1993). Comparison of the acyl chain specificities of human myristoyl-CoA synthetase and human myristoyl-CoA:protein N-myristoyltransferase. J Biol Chem 268, 4889-4902.

Lad, L., Schuller, D. J., Shimizu, H., Friedman, J., Li, H., Ortiz de Montellano, P. R., and Poulos, T. L. (2003a). Comparison of the heme-free and -bound crystal structures of human heme oxygenase-1. J Biol Chem 278, 7834-7843.

Lad, L., Wang, J., Li, H., Friedman, J., Bhaskar, B., Ortiz de Montellano, P. R., and Poulos, T. L. (2003b). Crystal structures of the ferric, ferrous, and ferrous-NO forms of the Asp140Ala mutant of human heme oxygenase-1: catalytic implications. J Mol Biol 330, 527-538.

Litvak, V., Ramsey, S. A., Rust, A. G., Zak, D. E., Kennedy, K. A., Lampano, A. E., Nykter, M., Shmulevich, I., and Aderem, A. (2009). Function of C/EBPdelta in a regulatory circuit that discriminates between transient and persistent TLR4-induced signals. Nat Immunol 10, 437-443.

Maines, M. D. (1988). Heme oxygenase: function, multiplicity, regulatory mechanisms, and clinical applications. FASEB J 2, 2557-2568.

Martinez, A., Traverso, J. A., Valot, B., Ferro, M., Espagne, C., Ephritikhine, G., Zivy, M., Giglione, C., and Meinnel, T. (2008). Extent of N-terminal modifications in cytosolic proteins from eukaryotes. Proteomics 8, 2809-2831.

Maurer-Stroh, S., Eisenhaber, B., and Eisenhaber, F. (2002). N-terminal N-myristoylation of proteins: prediction of substrate proteins from amino acid sequence. J Mol Biol 317, 541-557.

Negre O, et al., Gene Therapy of the β-Hemoglobinopathies by Lentiviral Transfer of the β(A(T87Q))-Globin Gene, Hum Gene Ther. 2016 February; 27(2): 148-65. doi: 10.1089/hum.2016.007.

O'Neill, L. A., Golenbock, D., and Bowie, A. G. (2013). The history of Toll-like receptors—redefining innate immunity. Nat Rev Immunol 13, 453-460.

Ono, A., and Freed, E. O. (1999). Binding of human immunodeficiency virus type 1 Gag to membrane: role of the matrix amino terminus. J Virol 73, 4136-4144.

Ono, A., Orenstein, J. M., and Freed, E. O. (2000). Role of the Gag matrix domain in targeting human immunodeficiency virus type 1 assembly. J Virol 74, 2855-2866.

Otwinowski, Z., and Minor, W. (1997). Processing of X-ray diffraction data collected in oscillation mode. Method Enzymol 276, 307-326.

Pal, R., Reitz, M. S., Jr., Tschachler, E., Gallo, R. C., Sarngadharan, M. G., and Veronese, F. D. (1990). Myristoylation of gag proteins of HIV-1 plays an important role in virus assembly. AIDS Res Hum Retroviruses 6, 721-730.

Palmiter, R. D., Gagnon, J., Vogt, V. M., Ripley, S., and Eisenman, R. N. (1978). The NH2-terminal sequence of the avian oncovirus gag precursor polyprotein (Pr76gag). Virology 91, 423-433.

Patwardhan, P., and Resh, M. D. (2010). Myristoylation and membrane binding regulate c-Src stability and kinase activity. Mol Cell Biol 30, 4094-4107.

Prawan, A., Kundu, J. K., and Surh, Y. J. (2005). Molecular basis of heme oxygenase-1 induction: implications for chemoprevention and chemoprotection. Antioxid Redox Signal 7, 1688-1703.

Rahman, M. N., Vlahakis, J. Z., Szarek, W. A., Nakatsu, K., and Jia, Z. (2008). X-ray crystal structure of human heme oxygenase-1 in complex with 1-(adamantan-1-yl)-2-(1 H-imidazol-1-yl)ethanone: a common binding mode for imidazole-based heme oxygenase-1 inhibitors. J Med Chem 51, 5943-5952.

Reil, H., Bukovsky, A. A., Gelderblom, H. R., and Gottlinger, H. G. (1998). Efficient HIV-1 replication can occur in the absence of the viral matrix protein. EMBO J 17, 2699-2708.

Rein, A., McClure, M. R., Rice, N. R., Luftig, R. B., and Schultz, A. M. (1986). Myristylation site in Pr65gag is essential for virus particle formation by Moloney murine leukemia virus. Proc Natl Acad Sci USA 83, 7246-7250.

Resh, M. D. (2004). A myristoyl switch regulates membrane binding of HIV-1 Gag. Proc Natl Acad Sci USA 101, 417-418.

Resh, M. D. (2005). Intracellular trafficking of HIV-1 Gag: how Gag interacts with cell membranes and makes viral particles. AIDS Rev 7, 84-91.

Resh, M. D., and Ling, H. P. (1990). Identification of a 32K plasma membrane protein that binds to the myristylated amino-terminal sequence of p60v-src. Nature 346, 84-86.

Rodrigues, A. et al. (2011). Production of Retroviral and Lentiviral Gene Therapy Vectors: Challenges in the Manufacturing of Lipid Enveloped Virus, Viral Gene Therapy, Dr. Ke Xu (Ed.), InTech, DOA: 10.5772/18615.

Rowe, D. C., McGettrick, A. F., Latz, E., Monks, B. G., Gay, N. J., Yamamoto, M., Akira, S., O'Neill, L. A., Fitzgerald, K. A., and Golenbock, D. T. (2006). The myristoylation of TRIF-related adaptor molecule is essential for Toll-like receptor 4 signal transduction. Proc Natl Acad Sci USA 103, 6299-6304.

Saad, J. S., Loeliger, E., Luncsford, P., Liriano, M., Tai, J., Kim, A., Miller, J., Joshi, A., Freed, E. O., and Summers, M. F. (2007). Point mutations in the HIV-1 matrix protein turn off the myristyl switch. J Mol Biol 366, 574-585.

Sabo, Y., Ehrlich, M., and Bacharach, E. (2011). The conserved YAGL motif in human metapneumovirus is required for higher-order cellular assemblies of the matrix protein and for virion production. Journal of virology 85, 6594-6609.

Sacre, S. M., Lundberg, A. M., Andreakos, E., Taylor, C., Feldmann, M., and Foxwell, B. M. (2007). Selective use of TRAM in lipopolysaccharide (LPS) and lipoteichoic acid (LTA) induced NF-kappaB activation and cytokine production in primary human cells: TRAM is an adaptor for LPS and LTA signaling. J Immunol 178, 2148-2154.

Saharia, A., Guittat, L., Crocker, S., Lim, A., Steffen, M., Kulkarni, S., and Stewart, S. A. (2008). Flap endonuclease 1 contributes to telomere stability. Current biology: CB 18, 496-500.

Sanjana, N. E., Shalem, O., and Zhang, F. (2014). Improved vectors and genome-wide libraries for CRISPR screening. Nature methods 11, 783-784.

Schauder, C. M., Wu, X., Saheki, Y., Narayanaswamy, P., Torta, F., Wenk, M. R., De Camilli, P., and Reinisch, K. M. (2014). Structure of a lipid-bound extended synaptotagmin indicates a role in lipid transfer. Nature 510, 552-555.

Schuller, D. J., Wilks, A., Ortiz de Montellano, P. R., and Poulos, T. L. (1999). Crystal structure of human heme oxygenase-1. Nat Struct Biol 6, 860-867.

Seta, F., Bellner, L., Rezzani, R., Regan, R. F., Dunn, M. W., Abraham, N. G., Gronert, K., and Laniado-Schwartzman, M. (2006). Heme oxygenase-2 is a critical determinant for execution of an acute inflammatory and reparative response. Am J Pathol 169, 1612-1623.

Soneoka, Y., Cannon, P. M., Ramsdale, E. E., Griffiths, J. C., Romano, G., Kingsman, S. M., and Kingsman, A. J. (1995). A transient three-plasmid expression system for the production of high titer retroviral vectors. Nucleic acids research 23, 628-633.

Swanson, D. A., Chang, J. T., Campochiaro, P. A., Zack, D. J., and Valle, D. (1998). Mammalian orthologs of *C. elegans* unc-119 highly expressed in photoreceptors. Invest Ophthalmol Vis Sci 39, 2085-2094.

Tiscornial, G. et al. (2006) "Production and Purification of Lentiviral Vectors," Nature Protocols 1, 241-245.

Thinon, E., Serwa, R. A., Broncel, M., Brannigan, J. A., Brassat, U., Wright, M. H., Heal, W. P., Wilkinson, A. J., Mann, D. J., and Tate, E. W. (2014). Global profiling of co- and post-translationally N-myristoylated proteomes in human cells. Nat Commun 5, 4919.

Wright, K. J., Baye, L. M., Olivier-Mason, A., Mukhopadhyay, S., Sang, L., Kwong, M., Wang, W., Pretorius, P. R., Sheffield, V. C., Sengupta, P., et al. (2011). An ARL3-UNC119-RP2 GTPase cycle targets myristoylated NPHP3 to the primary cilium. Genes Dev 25, 2347-2360.

Wright, M. H., Heal, W. P., Mann, D. J., and Tate, E. W. (2010). Protein myristoylation in health and disease. J Chem Biol 3, 19-35.

Yamamoto, M., Sato, S., Hemmi, H., Uematsu, S., Hoshino, K., Kaisho, T., Takeuchi, O., Takeda, K., and Akira, S. (2003). TRAM is specifically involved in the Toll-like receptor 4-mediated MyD88-independent signaling pathway. Nat Immunol 4, 1144-1150.

Yang, S. H., Shrivastav, A., Kosinski, C., Sharma, R. K., Chen, M. H., Berthiaume, L. G., Peters, L. L., Chuang, P. T., Young, S. G., and Bergo, M. O. (2005). N-myristoyltransferase 1 is essential in early mouse development. J Biol Chem 280, 18990-18995.

Zha, J., Weiler, S., Oh, K. J., Wei, M. C., and Korsmeyer, S. J. (2000). Posttranslational N-myristoylation of BID as a molecular switch for targeting mitochondria and apoptosis. Science 290, 1761-1765.

Zhang, H., Constantine, R., Vorobiev, S., Chen, Y., Seetharaman, J., Huang, Y. J., Xiao, R., Montelione, G. T., Gerstner, C. D., Davis, M. W., et al. (2011). UNC119 is required for G protein trafficking in sensory neurons. Nat Neurosci 14, 874-880.

Zhou, W., and Resh, M. D. (1996). Differential membrane binding of the human immunodeficiency virus type 1 matrix protein. J Virol 70, 8540-8548.

What is claimed is:

1. A method for producing viruses and increasing virus production from viral proteins in a cell, comprising adding a pharmaceutical reagent to the cell, wherein the pharmaceutical reagent reduces, inhibits or prevents Heme Oxygenase 2 (HO-2) from binding to the group-specific antigen (Gag) of the viral proteins, thus allowing delivery of the viral proteins to plasma membranes and increasing viral particle maturation and production.

2. The method of claim 1, wherein the Gag of the viral proteins carries a C14 myristate chain on the Matrix domain (MA).

3. A method for increasing virus production from viral proteins in a cell, comprising the use of genetic knockdown wherein the genetic knockdown reduces, inhibits or prevents Heme Oxygenase 2 (HO-2) from binding to the group-specific antigen (Gag) of the viral proteins, thus allowing delivery of the viral proteins to plasma membranes and increasing viral particle maturation and production.

4. The method of claim 3, wherein the genetic knockdown comprises preparation of a suitable siRNA or construction of an shRNA expression plasmid, followed by the transfection of one of these constructs into cultured cells.

5. The method of claim 3, wherein the genetic knockdown comprises introducing mutations.

6. The method of claim 1, wherein the pharmaceutical reagent is a noncleavable heme analogue.

7. The method of claim 6, wherein the heme analog is a transition metal protoporphyrin.

8. The method of claim 1, wherein the HO-2 is removed from contact with the group-specific antigen (Gag) of the viral proteins.

9. The method of claim 1, wherein the reduction or prevention of HO-2 binding is achieved by altering the hydrophobic channel.

10. The method of claim 7, wherein the transition metal protoporphyrin is tin protoporphyrin.

* * * * *